(12) United States Patent
Sakanishi et al.

(10) Patent No.: US 12,180,178 B2
(45) Date of Patent: Dec. 31, 2024

(54) HETEROARYL AZOLE COMPOUND AND PEST CONTROL AGENT

(71) Applicant: NIPPON SODA CO., LTD., Tokyo (JP)

(72) Inventors: Keita Sakanishi, Odawara (JP); Hikaru Aoyama, Odawara (JP); Daisuke Ushijima, Odawara (JP); Takao Iwasa, Odawara (JP); Norifumi Sakiyama, Odawara (JP); Maki Matsui, Odawara (JP)

(73) Assignee: NIPPON SODA CO., LTD., Tokyo (JP)

( * ) Notice: Subject to any disclaimer, the term of this patent is extended or adjusted under 35 U.S.C. 154(b) by 879 days.

(21) Appl. No.: 17/271,531

(22) PCT Filed: Sep. 2, 2019

(86) PCT No.: PCT/JP2019/034410
§ 371 (c)(1),
(2) Date: Feb. 25, 2021

(87) PCT Pub. No.: WO2020/050212
PCT Pub. Date: Mar. 12, 2020

(65) Prior Publication Data
US 2021/0269415 A1    Sep. 2, 2021

(30) Foreign Application Priority Data

Sep. 3, 2018   (JP) .................... 2018-164656
Nov. 29, 2018  (JP) .................... 2018-223136
Dec. 21, 2018  (JP) .................... 2018-240045
Mar. 27, 2019  (JP) .................... 2019-061850

(51) Int. Cl.
| | |
|---|---|
| *C07D 401/04* | (2006.01) |
| *A01N 43/50* | (2006.01) |
| *A01N 43/54* | (2006.01) |
| *A01N 43/653* | (2006.01) |
| *C07D 233/64* | (2006.01) |
| *C07D 401/14* | (2006.01) |

(52) U.S. Cl.
CPC .......... *C07D 401/04* (2013.01); *A01N 43/50* (2013.01); *A01N 43/54* (2013.01); *A01N 43/653* (2013.01); *C07D 233/64* (2013.01); *C07D 401/14* (2013.01)

(58) Field of Classification Search
CPC .. C07D 401/04; C07D 233/64; C07D 401/14; A01N 43/50; A01N 43/54; A01N 43/653; A61K 31/4439; A61K 31/444; A61K 31/506; A61P 33/00; A61P 33/14
See application file for complete search history.

(56) References Cited

U.S. PATENT DOCUMENTS

2005/0009834 A1    1/2005   Itoh et al.

FOREIGN PATENT DOCUMENTS

| WO | 97/46530 A1 | 12/1997 |
|---|---|---|
| WO | 02/090335 A1 | 11/2002 |
| WO | 2016/012395 A1 | 1/2016 |

OTHER PUBLICATIONS

Nov. 19, 2019 International Search Report issued in International Patent Application No. PCT/JP2019/034410.

*Primary Examiner* — Matthew P Coughlin
*Assistant Examiner* — Meghan C Heasley
(74) *Attorney, Agent, or Firm* — Oliff PLC

(57) ABSTRACT

A heteroaryl azole compound of the following formula (II):

(II)

an N-oxide compound, stereoisomer, tautomer or hydrate thereof, or a salt of any of these compounds. In the formula (II), $R^1$ represents a substituted or unsubstituted C1-6 alkyl-thio group or the like; $B^1$ represents a nitrogen atom or $CR^2$; $R^2$ represents a hydrogen atom, a substituted or unsubstituted C1-6 alkyl group or the like; $R^3$ represents a hydrogen atom, a substituted or unsubstituted C1-6 alkyl group or the like; R represents a substituted or unsubstituted C1-6 alkyl group or the like; A represents a carbon atom or a nitrogen atom; X represents a substituted or unsubstituted C1-6 alkyl group or the like; n represents a number of chemically acceptable X, and is an integer of 0 to 2; and X is the same or different when n is 2.

5 Claims, No Drawings

HETEROARYL AZOLE COMPOUND AND PEST CONTROL AGENT

TECHNICAL FIELD

The present invention relates to a heteroaryl azole compound and a pest control agent. More specifically, the present invention relates to a heteroaryl azole compound that has excellent insecticidal activity and/or miticidal activity, is excellent in safety, and may be industrially advantageously synthesized, and a pest control agent containing the same as an active ingredient. The present application claims the priority of Japanese Patent Application No. 2018-164656 filed on 3 Sep. 2018, Japanese Patent Application No. 2018-223136 filed on 29 Nov. 2018, Japanese Patent Application No. 2018-240045 filed on filed on 21 Dec. 2018, and Japanese Patent Application No. 2019-061850 filed on 27 Mar. 2019, the contents of which are incorporated herein.

BACKGROUND ART

Various compounds having insecticidal or miticidal activity have been proposed. For practical use of such compounds as agrochemicals, it is required not only to have sufficiently high efficacy but to be less likely to cause chemical resistance, to cause neither phytotoxicity to plants nor soil pollution, and to be low toxic to livestock, fishes, etc.

Patent document 1 discloses a compound of formula (A), formula (B), etc.

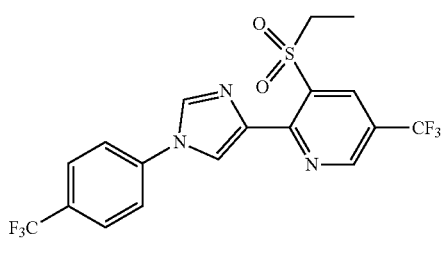

(A)

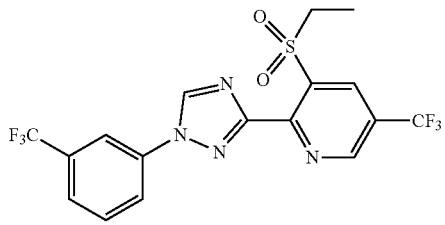

(B)

PRIOR ART DOCUMENTS

Patent Documents

Patent document 1: WO2016/012395

SUMMARY OF THE INVENTION

Object to be Solved by the Invention

An object of the present invention is to provide a heteroaryl azole compound that is excellent in pest control activity, particularly, insecticidal activity and/or miticidal activity, is excellent in safety, and may be industrially advantageously synthesized. Another object of the present invention is to provide a pest control agent, an insecticide or acaricide, an ectoparasite control agent, or an endoparasite control agent or expellant containing the heteroaryl azole compound as an active ingredient.

Means to Solve the Object

As a result of diligent studies to attain the objects, the present invention including the following form has been completed.

[1] A compound of formula (II), an N-oxide compound, stereoisomer, tautomer or hydrate thereof, or a salt of any of these compounds:

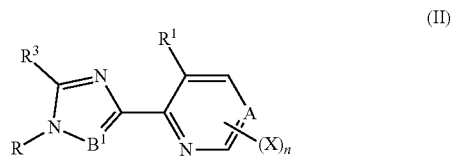

(II)

wherein
R$^1$ represents a substituted or unsubstituted C1-6 alkylthio group, a substituted or unsubstituted C1-6 alkylsulfinyl group or a substituted or unsubstituted C1-6 alkylsulfonyl group;
B$^1$ represents a nitrogen atom or CR$^2$;
R$^2$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted amino group, a cyano group or a halogeno group;
R$^3$ represents a hydrogen atom, a substituted or unsubstituted C1-6 alkyl group or a halogeno group;
R represents a substituted or unsubstituted C1-6 alkyl group, a substituted or unsubstituted C2-6 alkenyl group, a substituted or unsubstituted C2-6 alkynyl group, a substituted or unsubstituted C6-10 aryl group or a substituted or unsubstituted 5- to 6-membered heteroaryl group;
A represents a carbon atom or a nitrogen atom;
X represents a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C1-6 alkoxycarbonyl group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- to 6-membered heteroaryl group, a substituted or unsubstituted C6-10 aryloxy group, a substituted or unsubstituted 5- to 6-membered heteroaryloxy group, a substituted or unsubstituted amino group, a substituted or unsubstituted aminocarbonyl group, a substituted or unsubstituted hydrazinyl group, a nitro group, a cyano group or a halogeno group;
n represents the number of chemically acceptable Xs, and is an integer of 0 to 2; and
Xs are the same or different when n is 2.

[2] The compound according to [1], an N-oxide compound, stereoisomer, tautomer or hydrate thereof, or a salt of any of these compounds, wherein in the formula (II), R represents a C1-6 haloalkyl group, a C1-6 haloalkoxy C1-6 haloalkyl group, a C2-6 haloalkenyl group or a C1-6 haloalkoxy C2-6 haloalkenyl group.

[3] The compound according to [1], an N-oxide compound, stereoisomer, tautomer or hydrate thereof, or a salt of any of these compounds, wherein the formula (II) is the formula (IV):

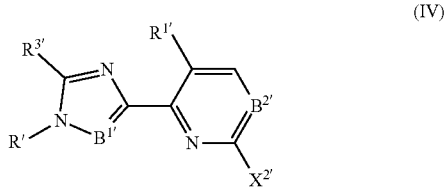

wherein
R$^{1'}$ represents a substituted or unsubstituted C1-6 alkylsulfonyl group;
B$^{1'}$ represents a nitrogen atom or CR$^{2'}$;
R$^{2'}$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted amino group, a cyano group or a halogeno group;
R$^{3'}$ represents a hydrogen atom, a substituted or unsubstituted C1-6 alkyl group or a halogeno group;
R' represents a substituted or unsubstituted C6-10 aryl group or a substituted or unsubstituted 5- to 6-membered heteroaryl group;
B$^{2'}$ represents a nitrogen atom or CX$^{1'}$;
X$^{1'}$ represents a hydrogen atom, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C1-6 alkoxycarbonyl group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- to 6-membered heteroaryl group, a substituted or unsubstituted C6-10 aryloxy group, a substituted or unsubstituted 5- to 6-membered heteroaryloxy group, a substituted or unsubstituted amino group, a substituted or unsubstituted aminocarbonyl group, a substituted or unsubstituted hydrazinyl group, a nitro group or a cyano group; and
X$^{2'}$ represents a hydrogen atom, a substituted or unsubstituted C1-6 alkyl group, a substituted or unsubstituted C2-6 alkenyl group, a substituted or unsubstituted C2-6 alkyl group, a hydroxy group, a substituted or unsubstituted C1-6 alkoxy group, a substituted or unsubstituted C1-6 alkoxycarbonyl group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- to 6-membered heteroaryl group, a substituted or unsubstituted C6-10 aryloxy group, a substituted or unsubstituted 5- to 6-membered heteroaryloxy group, a substituted or unsubstituted amino group, a substituted or unsubstituted aminocarbonyl group, a substituted or unsubstituted hydrazinyl group, a nitro group, a cyano group or a halogeno group,
with the proviso that both X$^{1'}$ and X$^{2'}$ are not hydrogen atoms at the same time.

[4] A pest control agent comprising at least one active ingredient selected from the group consisting of a compound according to any one of the above [1] to [3], an N-oxide compound, stereoisomer, tautomer and hydrate thereof and a salt of any of these compounds.

[5] An insecticide or acaricide comprising at least one active ingredient selected from the group consisting of a compound according to any one of the above [1] to [3], an N-oxide compound, stereoisomer, tautomer and hydrate thereof and a salt of any of these compounds.

[6] An ectoparasite control agent comprising at least one active ingredient selected from the group consisting of a compound according to any one of the above [1] to [3], an N-oxide compound, stereoisomer, tautomer and hydrate thereof and a salt of any of these compounds.

[7] An endoparasite control agent or expellant comprising at least one active ingredient selected from the group consisting of a compound according to any one of the above [1] to [3], an N-oxide compound, stereoisomer, tautomer and hydrate thereof and a salt of any of these compounds.

Effect of the Invention

The heteroaryl azole compound of the present invention of a salt thereof may control pests that are problems associated with crops or hygiene. Particularly, the heteroaryl azole compound of the present invention may effectively control agricultural insect pests and mites at a lower concentration. Furthermore, the heteroaryl azole compound of the present invention may effectively control ectoparasites and endoparasites harmful to humans and animals.

MODE OF CARRYING OUT THE INVENTION

[Heteroaryl Azole Compound]
The heteroaryl azole compound of the present invention is a compound of formula (II) (hereinafter, also referred to as compound (II)), an N-oxide compound, stereoisomer, tautomer or hydrate thereof, or a salt of any of these compounds. The compound of formula (II) includes every stereoisomer which is an enantiomer or a diastereomer.

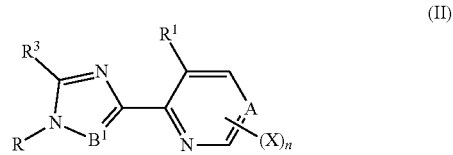

In the present invention, the term "unsubstituted" means a group consisting of only a mother nucleus. Only the name of a group consisting of a mother nucleus without the term "substituted" means an "unsubstituted" group unless otherwise specified.

On the other hand, the term "substituted" means that any hydrogen atom of a group consisting of a mother nucleus is substituted with a group (substituent) having a structure that is the same as or different from that of the mother nucleus. Thus, the "substituent" means another group bonded to the group consisting of a mother nucleus. The number of the substituent may be one or more. Two or more substituents are the same or different.

Terms such as "C1-6" mean that the number of carbon atoms in the group consisting of a mother nucleus is 1 to 6, etc. This number of carbon atoms does not include the number of carbon atoms present in the substituent. For example, a butyl group having an ethoxy group as a substituent is classified into a C2 alkoxy C4 alkyl group.

The "substituent" is not particularly limited as long as the substituent is chemically acceptable and produces the effect of the present invention. Hereinafter, a group capable of serving as the "substituent" is exemplified:

a C1-6 alkyl group such as a methyl group, an ethyl group, a n-propyl group, an i-propyl group, a n-butyl group, a s-butyl group, an i-butyl group, a t-butyl group, a n-pentyl group, and a n-hexyl group;

a C2-6 alkenyl group such as a vinyl group, a 1-propenyl group, a 2-propenyl group (allyl group), a 1-butenyl group, a 2-butenyl group, a 3-butenyl group, a 1-methyl-2-propenyl group, and a 2-methyl-2-propenyl group;

a C2-6 alkynyl group such as an ethynyl group, a 1-propynyl group, a 2-propynyl group, a 1-butynyl group, a 2-butynyl group, a 3-butynyl group, and a 1-methyl-2-propynyl group;

a C3-8 cycloalkyl group such as a cyclopropyl group, a cyclobutyl group, a cyclopentyl group, a cyclohexyl group, and a cubanyl group;

a C6-10 aryl group such as a phenyl group and a naphthyl group;

a C6-10 aryl C1-6 alkyl group such as a benzyl group and a phenethyl group;

a 3- to 6-membered heterocyclyl group;

a 3- to 6-membered heterocyclyl C1-6 alkyl group;

a hydroxy group;

a C1-6 alkoxy group such as a methoxy group, an ethoxy group, a n-propoxy group, an i-propoxy group, a n-butoxy group, a s-butoxy group, an i-butoxy group, and a t-butoxy group;

a C2-6 alkenyloxy group such as a vinyloxy group, an allyloxy group, a propenyloxy group, and a butenyloxy group;

a C2-6 alkynyloxy group such as an ethynyloxy group and a propargyloxy group;

a C6-10 aryloxy group such as a phenoxy group and a naphthoxy group;

a C6-10 aryl C1-6 alkoxy group such as a benzyloxy group and a phenethyloxy group;

a 5- or 6-membered heteroaryloxy group such as a thiazolyloxy group and a pyridyloxy group;

a 5- or 6-membered heteroaryl C1-6 alkyloxy group such as a thiazolylmethyloxy group and a pyridylmethyloxy group;

a formyl group;

a C1-6 alkylcarbonyl group such as an acetyl group and a propionyl group;

a formyloxy group;

a C1-6 alkylcarbonyloxy group such as an acetyloxy group and a propionyloxy group;

a C6-10 arylcarbonyl group such as a benzoyl group;

a C1-6 alkoxycarbonyl group such as a methoxycarbonyl group, an ethoxycarbonyl group, a n-propoxycarbonyl group, an i-propoxycarbonyl group, a n-butoxycarbonyl group, and a t-butoxycarbonyl group;

a C1-6 alkoxycarbonyloxy group such as a methoxycarbonyloxy group, an ethoxycarbonyloxy group, a n-propoxycarbonyloxy group, an i-propoxycarbonyloxy group, a n-butoxycarbonyloxy group, and a t-butoxycarbonyloxy group;

a carboxy group;

a halogeno group such as a fluoro group, a chloro group, a bromo group, and an iodo group;

a C1-6 haloalkyl group such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group, and a 2,4,6-trichlorohexyl group;

a C2-6 haloalkenyl group such as a 2-chloro-1-propenyl group and a 2-fluoro-1-butenyl group;

a C2-6 haloalkynyl group such as a 4,4-dichloro-1-butynyl group, a 4-fluoro-1-pentynyl group, and a 5-bromo-2-pentynyl group;

a C1-6 haloalkoxy group such as a trifluoromethoxy group, a 2-chloro-n-propoxy group, and a 2,3-dichlorobutoxy group;

a C2-6 haloalkenyloxy group such as a 2-chloropropenyloxy group and a 3-bromobutenyloxy group;

a C1-6 haloalkylcarbonyl group such as a chloroacetyl group, a trifluoroacetyl group, and a trichloroacetyl group;

an amino group;

a C1-6 alkyl-substituted amino group such as a methylamino group, a dimethylamino group, and a diethylamino group;

a C6-10 arylamino group such as an anilino group and a naphthylamino group;

a C6-10 aryl C1-6 alkylamino group such as a benzylamino group and a phenethylamino group;

a formylamino group;

a C1-6 alkylcarbonylamino group such as an acetylamino group, a propanoylamino group, a butyrylamino group, and an i-propylcarbonylamino group;

a C1-6 alkoxycarbonylamino group such as a methoxycarbonylamino group, an ethoxycarbonylamino group, a n-propoxycarbonylamino group, and an i-propoxycarbonylamino group;

an unsubstituted or substituted aminocarbonyl group such as an aminocarbonyl group, a dimethylaminocarbonyl group, a phenylaminocarbonyl group, and a N-phenyl-N-methylaminocarbonyl group;

an imino C1-6 alkyl group such as an iminomethyl group, a (1-imino)ethyl group, and a (1-imino)-n-propyl group;

a substituted or unsubstituted N-hydroxyimino C1-6 alkyl group such as a N-hydroxy-iminomethyl group, a (1-(N-hydroxy)-imino)ethyl group, a (1-(N-hydroxy)-imino)propyl group, a N-methoxy-iminomethyl group, and a (1-(N-methoxy)-imino)ethyl group;

a C1-6 alkoxyimino group such as a methoxyimino group, an ethoxyimino group, a n-propoxyimino group, an i-propoxyimino group, and a n-butoxyimino group;

an aminocarbonyloxy group;

a C1-6 alkyl-substituted aminocarbonyloxy group such as an ethylaminocarbonyloxy group and a dimethylaminocarbonyloxy group;

a mercapto group;
a C1-6 alkylthio group such as a methylthio group, an ethylthio group, a n-propylthio group, an i-propylthio group, a n-butylthio group, an i-butylthio group, a s-butylthio group, and a t-butylthio group;
a C1-6 haloalkylthio group such as a trifluoromethylthio group and a 2,2,2-trifluoroethylthio group;
a C6-10 arylthio group such as a phenylthio group and a naphthylthio group;
a 5- or 6-membered heteroarylthio group such as a thiazolylthio group and a pyridylthio group;
a C1-6 alkylsulfinyl group such as a methylsulfinyl group, an ethylsulfinyl group, and a t-butylsulfinyl group;
a C1-6 haloalkylsulfinyl group such as a trifluoromethylsulfinyl group and a 2,2,2-trifluoroethylsulfinyl group;
a C6-10 arylsulfinyl group such as a phenylsulfinyl group;
a 5- or 6-membered heteroarylsulfinyl group such as a thiazolylsulfinyl group and a pyridylsulfinyl group;
a C1-6 alkylsulfonyl group such as a methylsulfonyl group, an ethylsulfonyl group, and a t-butylsulfonyl group;
a C1-6 haloalkylsulfonyl group such as a trifluoromethylsulfonyl group and a 2,2,2-trifluoroethylsulfonyl group;
a C6-10 arylsulfonyl group such as a phenylsulfonyl group;
a 5- or 6-membered heteroarylsulfonyl group such as a thiazolylsulfonyl group and a pyridylsulfonyl group;
a C1-6 alkylsulfonyloxy group such as a methylsulfonyloxy group, an ethylsulfonyloxy group, and a t-butylsulfonyloxy group;
a C1-6 haloalkylsulfonyloxy group such as a trifluoromethylsulfonyloxy group and a 2,2,2-trifluoroethylsulfonyloxy group;
a tri-C1-6 alkyl-substituted silyl group such as a trimethylsilyl group, a triethylsilyl group, and a t-butyldimethylsilyl group;
a tri-C6-10 aryl-substituted silyl group such as a triphenylsilyl group;
a cyano group;
and a nitro group.

For these "substituents", any hydrogen atom in each substituent may be substituted with a group having a distinct structure. In this case, as the "substituent", a C1-6 alkyl group, a C1-6 haloalkyl group, a C1-6 alkoxy group, a C1-6 haloalkoxy group, a halogeno group, a cyano group, a nitro group or the like may be exemplified.

The "3- to 6-membered heterocyclyl group" described above contains 1 to 4 heteroatoms selected from the group consisting of a nitrogen atom, an oxygen atom and a sulfur atom as ring-constituting atoms. The heterocyclyl group may be either monocyclic or polycyclic. The polycyclic heterocyclyl group has at least one hetero ring, and the remaining ring(s) may be any of a saturated alicyclic ring, an unsaturated alicyclic ring and an aromatic ring. As the "3- to 6-membered heterocyclyl group", a 3- to 6-membered saturated heterocyclyl group, a 5- or 6-membered heteroaryl group, a 5- or 6-membered partially unsaturated heterocyclyl group or the like may be exemplified.

As the 3- to 6-membered saturated heterocyclyl group, an aziridinyl group, an epoxy group, a pyrrolidinyl group, a tetrahydrofuranyl group, a thiazolidinyl group, a piperidyl group, a piperazinyl group, a morpholinyl group, a dioxolanyl group, a dioxanyl group or the like may be exemplified.

As the 5-membered heteroaryl group, a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group or the like may be exemplified.

As the 6-membered heteroaryl group, a pyridyl group, a pyrazinyl group, a pyrimidinyl group, a pyridazinyl group, a triazinyl group or the like may be exemplified.

[$B^1$]

In the formula (II), $B^1$ represents a nitrogen atom or $CR^2$.

Specifically, the compound of formula (II) is a compound of formula (I) or formula (III).

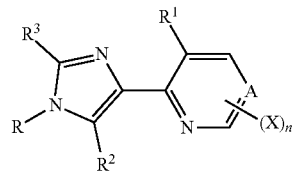

(I)

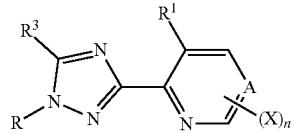

(III)

In the formula (I), $R^1$, $R^2$, $R^3$, R, A, X and n represent the same meanings as described in the formula (II). In the formula (III), $R^1$, $R^3$, R, A, X and n represent the same meanings as described in the formula (II).

[A]

In the formula (II), A represents a carbon atom or a nitrogen atom.

Specifically, the compound of formula (II) is a compound of the following formula (II-1) or formula (II-2)

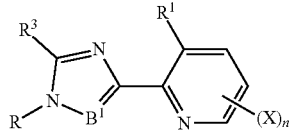

(II-1)

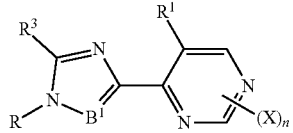

(II-2)

In the formula (II-1) and the formula (II-2), $R^1$, $R^3$, R, $B^1$, X and n represent the same meanings as described in the formula (II).

The compound of formula (II) is preferably a compound of formula (II-1).

Specifically, the compound of formula (II) is a compound of the following formula (I-1), formula (I-2), formula (III-1) or formula (III-2).

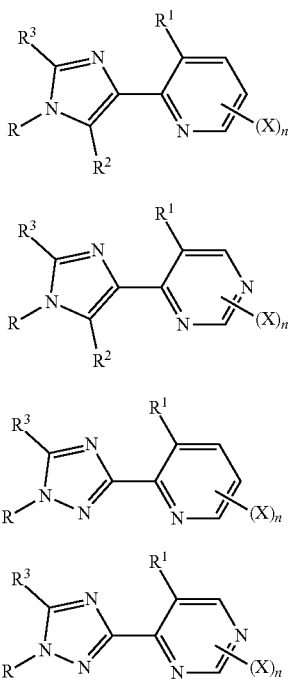

In the formula (I-1) and the formula (I-2), $R^1$, $R^2$, $R^3$, R, X and n represent the same meanings as described in the formula (II). In the formula (III-1) and the formula (III-2), $R^1$, $R^3$, R, X and n represent the same meanings as described in the formula (II).

The compound of formula (II) is preferably a compound of formula (I-1), the formula (III-1) or the formula (III-2), more preferably a compound of formula (I-1) or the formula (III-1).

[$R^1$]

In the formula (II), $R^1$ represents a substituted or unsubstituted C1-6 alkylthio group, a substituted or unsubstituted C1-6 alkylsulfinyl group or a substituted or unsubstituted C1-6 alkylsulfonyl group.

As the "C1-6 alkylthio group" represented by $R^1$, a methylthio group, an ethylthio group, a n-propylthio group, a n-butylthio group, a n-pentylthio group, a n-hexylthio group, an i-propylthio group, an i-butylthio group or the like may be exemplified.

As the "C1-6 alkylsulfinyl group" represented by $R^1$, a methylsulfinyl group, an ethylsulfinyl group, a t-butylsulfinyl group or the like may be exemplified.

As the "C1-6 alkylsulfonyl group" represented by $R^1$, a methylsulfonyl group, an ethylsulfonyl group, a t-butylsulfonyl group or the like may be exemplified.

As the substituents on the "C1-6 alkylthio group", "C1-6 alkylsulfinyl group" and the "C1-6 alkylsulfonyl group" represented by $R^1$, a halogeno group such as a fluoro group, a chloro group, a bromo group, and an iodo group may be preferably exemplified.

$R^1$ is preferably a C1-6 alkylsulfonyl group.

[$R^2$]

In the formula (II), $R^2$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted amino group, a cyano group or a halogen group.

The "C1-6 alkyl group" represented by $R^2$ may be linear or branched. As the "C1-6 alkyl group", a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, an i-hexyl group or the like may be exemplified.

As the "C2-6 alkenyl group" represented by $R^2$, a vinyl group, a 1-methylvinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group or the like may be exemplified.

As the "C2-6 alkynyl group" represented by $R^2$, an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, a 1,1-dimethyl-2-butynyl group or the like may be exemplified.

As the substituents on the "C1-6 alkyl group", the "C2-6 alkenyl group" and the "C2-6 alkynyl group" represented by $R^2$, halogeno groups such as a fluoro group, a chloro group, a bromo group and an iodo group may be preferably exemplified.

The "substituted or unsubstituted amino group" represented by $R^2$ is a group represented by "—$NR^aR^b$". As $R^a$ and $R^b$ in the formula, each independently, a hydrogen atom, a C1-6 alkyl group, a formyl group, a C1-6 alkylcarbonyl group, a substituted or unsubstituted aminocarbonyl group, a group represented by "—C(=NH)$NR^fR^g$", or the like may be exemplified.

As the "C1-6 alkyl group" represented by each of $R^a$ and $R^b$, the same group as exemplified for $R^2$ above is exemplified.

As the "C1-6 alkylcarbonyl group" represented by each of $R^a$ and $R^b$, an acetyl group, a propionyl group or the like may be exemplified.

As the "substituted or unsubstituted aminocarbonyl group" represented by each of $R^a$ and $R^b$, an aminocarbonyl group, a methylaminocarbonyl group, an ethylaminocarbonyl group, a dimethylaminocarbonyl group or the like may be exemplified.

$R^f$ and $R^g$ in the group represented by "—C(=NH)$NR^fR^g$" represented by each of $R^a$ and $R^b$ each independently represent a hydrogen atom, a C1-6 alkyl group, a formyl group or a C1-6 alkylcarbonyl group.

As the "C1-6 alkyl group" represented by each of $R^f$ and $R^g$, the same group as exemplified for $R^2$ above is exemplified.

As the "C1-6 alkylcarbonyl group" represented by each of $R^f$ and $R^g$, the same group as exemplified for each of $R^a$ and $R^b$ above is exemplified.

As the "halogeno group" represented by $R^2$, a fluoro group, a chloro group, a bromo group, an iodo group or the like may be exemplified.

$R^2$ is preferably a hydrogen atom, a C1-6 alkyl group or a halogeno group.

[$R^3$]

In the formula (II), $R^3$ is a hydrogen atom, a substituted or unsubstituted C1-6 alkyl group or a halogeno group.

As the "substituted or unsubstituted C1-6 alkyl group" and the "halogeno group" represented by $R^3$, the same groups as exemplified for $R^2$ above are exemplified.

$R^3$ is preferably a hydrogen atom.

[R]

In the formula (II), R represents a substituted or unsubstituted C1-6 alkyl group, a substituted or unsubstituted C2-6 alkenyl group, a substituted or unsubstituted C2-6 alkynyl group, a substituted or unsubstituted C6-10 aryl group or a substituted or unsubstituted 5- to 6-membered heteroaryl group.

As the "C1-6 alkyl group", the "C2-6 alkenyl group" and the "C2-6 alkynyl group" represented by R, the same groups as exemplified for $R^2$ above are exemplified.

As the "substituted C1-6 alkyl group" represented by R, a C1-6 haloalkyl group such as a fluoromethyl group, a difluoromethyl group, a trifluoromethyl group, a 2,2,2-trifluoromethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,4,4,4-hexafluorobutyl group, a 2,2,3,3,4,4,4-heptafluorobutyl group, a perfluorobutyl group, a 2,2,3,3,4,4,5,5-octafluoropentyl group, a 2,2,3,3,4,4,5,5,5-nonafluoropentyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group or a 2,4,6-trichlorohexyl group; a C1-6 haloalkoxy C1-6 haloalkyl group such as a 1,1,2-trifluoro-2-(trifluoromethoxy)ethyl group or a 1,1,2-trifluoro-2-(perfluoropropoxy)ethyl group; or a benzyl group may be exemplified.

As the "substituted C2-6 alkenyl group" represented by R, a C2-6 haloalkenyl group such as a 2-fluoro-2-bromovinyl group, a 2,2-dichlorovinyl group, a 2-chloro-2-iodovinyl group, a 2-chloro-1-propenyl group, a 2,3,3,3-tetrafluoro-1-propenyl group, a 3,3,3-trifluoro-1-propenyl group, a 2-chloro-3,3,3-trifluoro-1-propenyl group, a 3,3,3-trifluoro-2-trifluoromethyl-1-propenyl group, a 2-fluoro-1-butenyl group, a 3,3,4,4,4-pentafluoro-1-butenyl group, 2,3,4,4,4-pentafluoro-1-butenyl group, a 2,3,3,4,4,4-hexafluoro-1-butenyl group, a 2-chloro-3,3,4,4,4-pentafluoro-1-butenyl group, 2,3,3,4,4,5,5-heptafluoro-1-pentenyl group, a 3,3,4,4,5,5,5-heptafluoro-1-pentenyl group, a 2-chloro-3,3,4,4,5,5,5-heptafluoro-1-pentenyl group, a 2,3,3,4,4,5,5,5-octafluoro-1-pentenyl group, and a 3,3,4,4,5,5,6,6,6-nonafluoro-1-hexenyl group; and a C1-6 haloalkoxy C2-6 haloalkenyl group such as a 1,2-difluoro-2-(perfluoropropoxy)vinyl group may be exemplified.

As the substituents on the "C1-6 alkyl group", the "C2-6 alkenyl group" and the "C2-6 alkynyl group" represented by R, halogeno groups such as a fluoro group, a chloro group, a bromo group and an iodo group; and C1-6 haloalkoxy groups such as a trifluoromethoxy group, a perfluoroethoxy group, a 2-chloro-n-propoxy group, a perfluoropropoxy group and a 2,3-dichlorobutoxy group may be preferably exemplified.

The "C6-10 aryl group" represented by R may be either monocyclic or polycyclic. The polycyclic aryl group has at least one aromatic ring, and the remaining ring(s) may be any of a saturated alicyclic ring, an unsaturated alicyclic ring and an aromatic ring. As the "C6-10 aryl group", a phenyl group, a naphthyl group, an azulenyl group, an indenyl group, an indanyl group, a tetralinyl group or the like is exemplified.

As the "5- to 6-membered heteroaryl group" represented by R, a 5-membered heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group (specifically, a [1,2,3]triazolyl group or a [1,2,4]triazolyl group), an oxadiazolyl group (specifically, a [1,2,3]oxadiazolyl group, a [1,2,4]oxadiazolyl group, a [1,2,5]oxadiazolyl group or a [1,3,4]oxadiazolyl group), a thiadiazolyl group or a tetrazolyl group; or a 6-membered heteroaryl group such as a pyridyl group, a pyrazinyl group, a pyrimidinyl group, a pyridazinyl group or a triazinyl group may be exemplified.

As the substituents on the "C6-10 aryl group" and the "5- to 6-membered heteroaryl group" represented by R, halogeno groups such as a fluoro group, a chloro group, a bromo group and an iodo group; C1-6 alkyl groups such as a methyl group, an ethyl group, a n-propyl group, an i-propyl group, a n-butyl group, a s-butyl group, an i-butyl group, a t-butyl group, a n-pentyl group and a n-hexyl group; C1-6 haloalkyl groups such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group and a 2,4,6-trichlorohexyl group; C1-6 alkoxy groups such as a methoxy group, an ethoxy group, a n-propoxy group, an i-propoxy group, a n-butoxy group, a s-butoxy group, an i-butoxy group and a t-butoxy group; C1-6 haloalkoxy groups such as a 2-chloro-n-propoxy group, a 2,3-dichlorobutoxy group, a trifluoromethoxy group and a 1,1,2,2-tetrafluoroethoxy group; and C1-6 haloalkylthio groups such as a trifluoromethylthio group and a 2,2,2-trifluoroethylthio group may be exemplified.

R in the formula (II) is preferably a C1-6 haloalkyl group, a C1-6 haloalkoxy C1-6 haloalkyl group, a C2-6 haloalkenyl group or a C1-6 haloalkoxy C2-6 haloalkenyl group.

[X]

In the formula (II), X is a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C1-6 alkoxycarbonyl group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- to 6-membered heteroaryl group, a substituted or unsubstituted C6-10 aryloxy group, a substituted or unsubstituted 5- to 6-membered heteroaryloxy group, a substituted or unsubstituted amino group, a substituted or unsubstituted aminocarbonyl group, a substituted or unsubstituted hydrazinyl group, a nitro group, a cyano group or a halogeno group.

As the "substituted or unsubstituted C1-6 alkyl group", the "substituted or unsubstituted C2-6 alkenyl group", the "substituted or unsubstituted C2-6 alkynyl group", the "substituted or unsubstituted amino group" and the "halogeno group" represented by X, the same groups as exemplified for $R^2$ above are exemplified.

As the "substituted or unsubstituted C1-6 alkylthio group", the "substituted or unsubstituted C1-6 alkylsulfinyl group" and the "substituted or unsubstituted C1-6 alkylsulfonyl group" represented by X, the same groups as exemplified for $R^1$ above are exemplified.

As the "substituted or unsubstituted C6-10 aryl group" and the "substituted or unsubstituted 5- to 6-membered heteroaryl group", the same groups as exemplified for R above are exemplified.

As the "C1-6 alkoxy group" represented by X, a methoxy group, an ethoxy group, a n-propoxy group, an i-propoxy group, a n-butoxy group, a s-butoxy group, an i-butoxy group, a t-butoxy group or the like may be exemplified.

As the "C1-6 alkoxycarbonyl group" represented by X, a methoxycarbonyl group, an ethoxycarbonyl group, a n-propoxycarbonyl group, an i-propoxycarbonyl group, a n-butoxycarbonyl group, a t-butoxycarbonyl group or the like may be exemplified.

As the substituent on the "C1-6 alkyl group" represented by X, a halogeno group such as a fluoro group, a chloro group, a bromo group or an iodo group; a C1-6 alkoxy group such as a methoxy group, an ethoxy group, a n-propoxy group, an i-propoxy group, a n-butoxy group, a s-butoxy group, an i-butoxy group or a t-butoxy group; or a C1-6 alkoxyimino group such as a methoxyimino group, an ethoxyimino group, a n-propoxyimino group, an i-propoxyimino group or a n-butoxyimino group may be preferably exemplified.

As the substituents on the "C2-6 alkenyl group", the "C2-6 alkynyl group", the "C1-6 alkoxy group", the "C1-6 alkylthio group", the "C1-6 alkylsulfinyl group" and the "C1-6 alkylsulfonyl group" represented by X, halogeno groups such as a fluoro group, a chloro group, a bromo group and an iodo group; and C1-6 alkoxy groups such as a methoxy group, an ethoxy group, a n-propoxy group, an i-propoxy group, a n-butoxy group, a s-butoxy group, an i-butoxy group and a t-butoxy group may be preferably exemplified.

As the "C3-8 cycloalkyl group" represented by X, a cyclopropyl group, a cyclobutyl group, a cyclopentyl group, a cyclohexyl group, a cubanyl group or the like may be exemplified.

As the "C6-10 aryloxy group" represented by X, a phenoxy group, a naphthyloxy group or the like may be exemplified.

As the "5- to 6-membered heteroaryloxy group" represented by X, a pyridyloxy group, a pyrimidyloxy group or the like may be exemplified.

The substituents on the "C3-8 cycloalkyl group", the "C6-10 aryl group", the "5- to 6-membered heteroaryl group", the "C6-10 aryloxy group" and the "5- to 6-membered heteroaryloxy group" represented by X, halogeno groups such as a fluoro group, a chloro group, a bromo group and an iodo group; C1-6 alkyl groups such as a methyl group, an ethyl group, a n-propyl group, an i-propyl group, a n-butyl group, a s-butyl group, an i-butyl group, a t-butyl group, a n-pentyl group and a n-hexyl group; C1-6 haloalkyl groups such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group and a 2,4,6-trichlorohexyl group; C1-6 alkoxy groups such as a methoxy group, an ethoxy group, a n-propoxy group, an i-propoxy group, a n-butoxy group, a s-butoxy group, an i-butoxy group and a t-butoxy group; and C1-6 haloalkoxy groups such as a 2-chloro-n-propoxy group, a 2,3-dichlorobutoxy group and a trifluoromethoxy group may be preferably exemplified, and halogeno groups or C1-6 alkyl groups are more preferable.

As the "substituted or unsubstituted aminocarbonyl group" represented by X, the same group as exemplified for $R^a$ and $R^b$ above is exemplified.

The "substituted or unsubstituted hydrazinyl group" represented by X is a group represented by the formula (a)

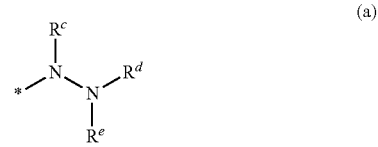

(a)

In the formula (a), * represents a binding position, $R^c$, $R^d$ and $R^e$ each independently represent a hydrogen atom, a C1-6 alkyl group, a substituted or unsubstituted phenylsulfonyl group or the like.

As the "C1-6 alkyl group" represented by each of $R^c$, $R^d$ and $R^e$, the same group as exemplified for X above is exemplified.

As the "substituted phenylsulfonyl group" represented by $R^c$, $R^d$ and $R^e$, a paratoluenesulfonyl group or the like may be exemplified.

X is preferably a substituted or unsubstituted C1-6 alkyl group, a substituted or unsubstituted C2-6 alkenyl group, a substituted or unsubstituted C1-6 alkoxy group, a substituted or unsubstituted C3-8 cycloalkyl group, a substituted or unsubstituted C1-6 alkylsulfonyl group, a substituted or unsubstituted C6-10 aryl group, a substituted or unsubstituted 5- to 6-membered heteroaryl group, a substituted or unsubstituted C6-10 aryloxy group or a substituted or unsubstituted 5- to 6-membered heteroaryloxy group, more preferably a substituted or unsubstituted C1-6 alkyl group, a substituted or unsubstituted C3-8 cycloalkyl group, a substituted or unsubstituted C6-10 aryl group or a substituted or unsubstituted 5- to 6-membered heteroaryl group.

[n]

n represents a number of chemically acceptable X, and is an integer of 0 to 2; and X is the same or different when n is 2.

n is preferably 0 to 1.

[Salt]

The salt of the compound (II) is not particularly limited as long as the salt is agriculturally or horticulturally acceptable. As the salt of the compound (I), for example, a salt of an inorganic acid such as hydrochloric acid and sulfuric acid; a salt of an organic acid such as acetic acid and lactic acid; a salt of an alkali metal such as lithium, sodium and potassium; a salt of an alkaline earth metal such as calcium and magnesium; a salt of a transition metal such as iron and copper; a salt of an organic base such as triethylamine, tributylamine, pyridine, and hydrazine; ammonia; or the like may be exemplified.

[Production Method]

The method for producing the compound (II) or the salt of the compound (II) is not particularly limited. For example, the compound (II) or the salt of the compound (II) of the present invention may be obtained by known methods described in Examples, etc. Alternatively, the salt of the compound (II) may be obtained by a known approach from the compound (II).

[Compound of Formula (IV)]

The compound of formula (II) is preferably a compound of formula (IV).

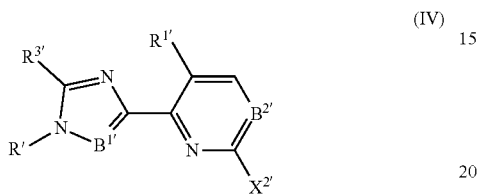

wherein
- $R^{1'}$ represents a substituted or unsubstituted C1-6 alkylsulfonyl group;
- $B^{1'}$ represents a nitrogen atom or $CR^{2'}$;
- $R^{2'}$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted amino group, a cyano group or a halogeno group;
- $R^{3'}$ represents a hydrogen atom, a substituted or unsubstituted C1-6 alkyl group or a halogeno group;
- R' represents a substituted or unsubstituted C6-10 aryl group or a substituted or unsubstituted 5- to 6-membered heteroaryl group;
- $B^{2'}$ represents a nitrogen atom or $CX^{1'}$;
- $X^{1'}$ represents a hydrogen atom, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C1-6 alkoxycarbonyl group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- to 6-membered heteroaryl group, a substituted or unsubstituted C6-10 aryloxy group, a substituted or unsubstituted 5- to 6-membered heteroaryloxy group, a substituted or unsubstituted amino group, a substituted or unsubstituted aminocarbonyl group, a substituted or unsubstituted hydrazinyl group, a nitro group or a cyano group; and
- $X^{2'}$ represents a hydrogen atom, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C1-6 alkoxycarbonyl group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- to 6-membered heteroaryl group, a substituted or unsubstituted C6-10 aryloxy group, a substituted or unsubstituted 5- to 6-membered heteroaryloxy group, a substituted or unsubstituted amino group, a substituted or unsubstituted aminocarbonyl group, a substituted or unsubstituted hydrazinyl group, a nitro group, a cyano group or a halogeno group, with the proviso that both $X^{1'}$ and $X^{2'}$ are not hydrogen atoms at the same time.

[$B^{1'}$]

In the formula (IV), $B^{1'}$ represents a nitrogen atom or $CR^{2'}$.

Specifically, the compound of formula (IV) is a compound of formula (IV-1) or the formula (IV-2).

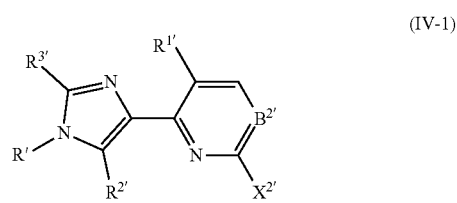

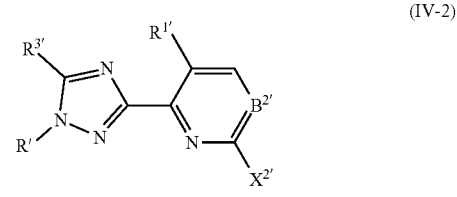

In the formula (IV-1), $R^{1'}$, $R^{2'}$, $R^{3'}$, R', $B^{2'}$, $X^{1'}$ and $X^{2'}$ represent the same meanings as described in the formula (IV). In the formula (IV-2), $R^{1'}$, $R^{3'}$, R', $B^{2'}$, $X^{1'}$ and $X^{2'}$ represent the same meanings as described in the formula (IV).

[$R^{1'}$]

In the formula (IV), $R^{1'}$ represents a substituted or unsubstituted C1-6 alkylsulfonyl group.

As the "C1-6 alkylsulfonyl group" represented by $R^{1'}$, a methylsulfonyl group, an ethylsulfonyl group, a t-butylsulfonyl group or the like may be exemplified.

As the substituent on the "C1-6 alkylsulfonyl group" represented by $R^{1'}$, a halogeno group such as a fluoro group, a chloro group, a bromo group or an iodo group may be preferably exemplified.

$R^{1'}$ is preferably a C1-6 alkylsulfonyl group.

[$R^{2'}$]

In the formula (IV), $R^{2'}$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted amino group, a cyano group or a halogeno group.

The "C1-6 alkyl group" represented by $R^{2'}$ may be linear or branched. As the "C1-6 alkyl group", a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, an i-hexyl group or the like may be exemplified.

As the "C2-6 alkenyl group" represented by $R^{2'}$, a vinyl group, a 1-methylvinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group or the like may be exemplified.

As the "C2-6 alkynyl group" represented by $R^{2'}$, an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, a 1,1-dimethyl-2-butynyl group or the like may be exemplified.

As the substituents on the "C1-6 alkyl group", the "C2-6 alkenyl group" and the "C2-6 alkynyl group" represented by $R^{2'}$, halogeno groups such as a fluoro group, a chloro group, a bromo group and an iodo group may be preferably exemplified.

The "substituted or unsubstituted amino group" represented by $R^{2'}$ is a group represented by "—$NR^aR^b$". As $R^a$ and $R^b$ in the formula, each independently, a hydrogen atom, a C1-6 alkyl group, a formyl group, a C1-6 alkylcarbonyl group, a substituted or unsubstituted aminocarbonyl group or the like may be exemplified.

As the "C1-6 alkyl group" represented by each of $R^a$ and $R^b$, the same group as exemplified for $R^{2'}$ above is exemplified.

As the "C1-6 alkylcarbonyl group" represented by each of $R^a$ and $R^b$, an acetyl group, a propionyl group or the like may be exemplified.

As the "substituted or unsubstituted aminocarbonyl group" represented by each of $R^a$ and $R^b$, an aminocarbonyl group, a methylaminocarbonyl group, an ethylaminocarbonyl group, a dimethylaminocarbonyl group or the like may be exemplified.

As the "halogeno group" represented by $R^{2'}$, a fluoro group, a chloro group, a bromo group, an iodo group or the like may be exemplified.

$R^{2'}$ is preferably a hydrogen atom, a C1-6 alkyl group or a halogeno group.

[$R^{3'}$]

In the formula (IV), $R^{3'}$ represents a hydrogen atom, a substituted or unsubstituted C1-6 alkyl group or a halogeno group.

As the "substituted or unsubstituted C1-6 alkyl group" and the "halogeno group" represented by $R^{3'}$, the same groups as exemplified for $R^{2'}$ above are exemplified.

$R^{3'}$ is preferably a hydrogen atom.

[R']

In the formula (IV), R' represents a substituted or unsubstituted C6-10 aryl group or a substituted or unsubstituted 5- to 6-membered heteroaryl group.

The "C6-10 aryl group" represented by R' may be either monocyclic or polycyclic. The polycyclic aryl group has at least one aromatic ring, and the remaining ring(s) may be any of a saturated alicyclic ring, an unsaturated alicyclic ring and an aromatic ring. As the "C6-10 aryl group", a phenyl group, a naphthyl group, an azulenyl group, an indenyl group, an indanyl group, a tetralinyl group or the like is exemplified.

As the "5- to 6-membered heteroaryl group" represented by R', a 5-membered heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group (specifically, a [1,2,3]triazolyl group or a [1,2,4]triazolyl group), an oxadiazolyl group (specifically, a [1,2,3]oxadiazolyl group, a [1,2,4]oxadiazolyl group, a [1,2,5]oxadiazolyl group or a [1,3,4]oxadiazolyl group), a thiadiazolyl group or a tetrazolyl group; or a 6-membered heteroaryl group such as a pyridyl group, a pyrazinyl group, a pyrimidinyl group, a pyridazinyl group or a triazinyl group may be exemplified.

As the substituents on the "C6-10 aryl group" and the "5- to 6-membered heteroaryl group" represented by R', halogeno groups such as a fluoro group, a chloro group, a bromo group and an iodo group; C1-6 alkyl groups such as a methyl group, an ethyl group, a n-propyl group, an i-propyl group, a n-butyl group, a s-butyl group, an i-butyl group, a t-butyl group, a n-pentyl group and a n-hexyl group; C1-6 haloalkyl groups such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group and a 2,4,6-trichlorohexyl group; C1-6 alkoxy groups such as a methoxy group, an ethoxy group, a n-propoxy group, an i-propoxy group, a n-butoxy group, a s-butoxy group, an i-butoxy group and a t-butoxy group; C1-6 haloalkoxy groups such as a 2-chloro-n-propoxy group, a 2,3-dichlorobutoxy group, a trifluoromethoxy group and a 1,1,2,2-tetrafluoroethoxy group; and C1-6 haloalkylthio groups such as a trifluoromethylthio group and a 2,2,2-trifluoroethylthio group may be preferably exemplified, and C1-6 haloalkyl groups and C1-6 haloalkoxy groups may be more preferably exemplified.

R' is preferably a substituted or unsubstituted phenyl group or a substituted or unsubstituted 5- to 6-membered heteroaryl group, more preferably a substituted or unsubstituted phenyl group or a substituted or unsubstituted pyridyl group.

[$B^{2'}$]

In the formula (IV), $B^{2'}$ represents a nitrogen atom or $CX^{1'}$.

Specifically, the compound of formula (IV) is a compound of formula (IV-3) or the formula (IV-4).

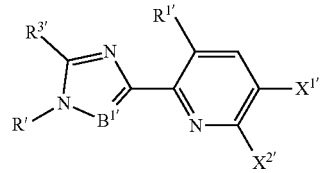

(IV-3)

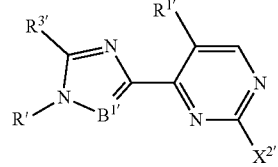

(IV-4)

In the formula (IV-3), $R^{1'}$, $R^{3'}$, R', $B^{1'}$, $X^{1'}$ and $X^{2'}$ represent the same meanings as described in the formula (IV). In the formula (IV-4), $R^{1'}$, $R^{3'}$, R', $B^{1'}$ and $X^{2'}$ represent the same meanings as described in the formula (IV).

Specifically, the compound of formula (IV) is a compound of formula (IV-5), the formula (IV-6), the formula (IV-7) or the formula (IV-8).

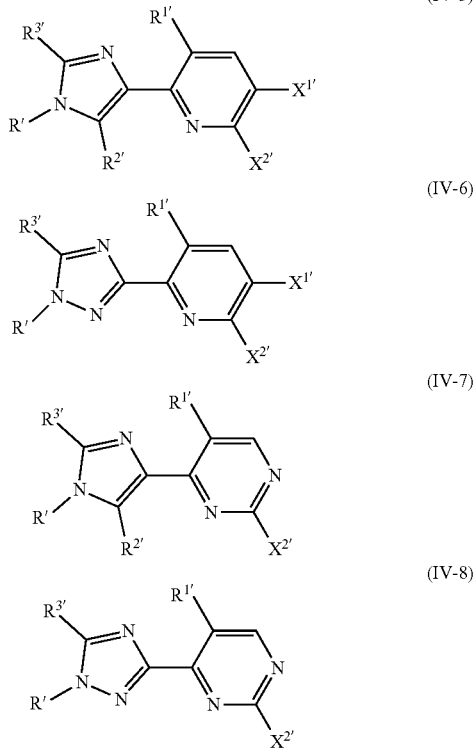

In the formula (IV-5), $R^{1'}$, $R^{2'}$, $R^{3'}$, R', $X^{1'}$ and $X^{2'}$ represent the same meanings as described in the formula (IV). In the formula (IV-6), $R^{1'}$, $R^{3'}$, R', $X^{1'}$ and $X^{2'}$ represent the same meanings as described in the formula (IV). In the formula (IV-7), $R^{1'}$, $R^{2'}$, $R^{3'}$, R' and $X^{2'}$ represent the same meanings as described in the formula (IV). In the formula (IV-8), $R^{1'}$, $R^{3'}$, R' and $X^{2'}$ represent the same meanings as described in the formula (IV).

The compound of formula (IV) is preferably a compound of formula (IV-5) or the formula (IV-6).

The compound of formula (IV) is preferably a compound of formula (IV-8).

[$X^{1'}$]

In the formula (IV), $X^{1'}$ represents a hydrogen atom, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C1-6 alkoxycarbonyl group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- to 6-membered heteroaryl group, a substituted or unsubstituted C6-10 aryloxy group, a substituted or unsubstituted 5- to 6-membered heteroaryloxy group, a substituted or unsubstituted amino group, a substituted or unsubstituted aminocarbonyl group, a substituted or unsubstituted hydrazinyl group, a nitro group or a cyano group.

As the "substituted or unsubstituted C1-6 alkylsulfonyl group" represented by $X^{1'}$, the same group as exemplified for $R^{1'}$ above is exemplified.

As the "substituted or unsubstituted C2-6 alkenyl group", the "substituted or unsubstituted C2-6 alkynyl group" and the "substituted or unsubstituted amino group" represented by $X^{1'}$, the same groups as exemplified for $R^{2'}$ above are exemplified.

As the "substituted or unsubstituted C6-10 aryl group" and the "substituted or unsubstituted 5- to 6-membered heteroaryl group" represented by $X^{1'}$, the same groups as exemplified for R' above are exemplified.

As the "C1-6 alkoxy group" represented by $X^{1'}$, a methoxy group, an ethoxy group, a n-propoxy group, an i-propoxy group, a n-butoxy group, a s-butoxy group, an i-butoxy group, a t-butoxy group or the like may be exemplified.

As the "C1-6 alkoxycarbonyl group" represented by $X^{1'}$, a methoxycarbonyl group, an ethoxycarbonyl group, a n-propoxycarbonyl group, an i-propoxycarbonyl group, a n-butoxycarbonyl group, a t-butoxycarbonyl group or the like may be exemplified.

As the "C1-6 alkylthio group" represented by $X^{1'}$, a methylthio group, an ethylthio group, a n-propylthio group, a n-butylthio group, a n-pentylthio group, a n-hexylthio group, an i-propylthio group, an i-butylthio group or the like may be exemplified.

As the "C1-6 alkylsulfinyl group" represented by $X^{1'}$, a methylsulfinyl group, an ethylsulfinyl group, a t-butylsulfinyl group or the like may be exemplified.

As the substituents on the "C1-6 alkoxy group", the "C1-6 alkoxycarbonyl group", the "C1-6 alkylthio group", the "C1-6 alkylsulfinyl group" and the "C1-6 alkylsulfonyl group" represented by $X^{1'}$, halogeno groups such as a fluoro group, a chloro group, a bromo group and an iodo group; and C1-6 alkoxy groups such as a methoxy group, an ethoxy group, a n-propoxy group, an i-propoxy group, a n-butoxy group, a s-butoxy group, an i-butoxy group and a t-butoxy group may be preferably exemplified.

As the "C3-8 cycloalkyl group" represented by $X^{1'}$, a cyclopropyl group, a cyclobutyl group, a cyclopentyl group, a cyclohexyl group, a cubanyl group or the like may be exemplified.

As the "C6-10 aryloxy group" represented by $X^{1'}$, a phenoxy group, a naphthyloxy group or the like may be exemplified.

As the "5- to 6-membered heteroaryloxy group" represented by $X^{1'}$, a pyridyloxy group, a pyrimidyloxy group or the like may be exemplified.

As the substituents on the "C3-8 cycloalkyl group", the "C6-10 aryl group", the "5- to 6-membered heteroaryl group", the "C6-10 aryloxy group" and the "5- to 6-membered heteroaryloxy group" represented by $X^{1'}$, halogeno groups such as a fluoro group, a chloro group, a bromo group and an iodo group; C1-6 alkyl groups such as a methyl group, an ethyl group, a n-propyl group, an i-propyl group, a n-butyl group, a s-butyl group, an i-butyl group, a t-butyl group, a n-pentyl group and a n-hexyl group; C1-6 haloalkyl groups such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group and a 2,4,6-trichlorohexyl group; C1-6 alkoxy groups such as a methoxy group, an ethoxy group, a n-propoxy group, an i-propoxy group, a n-butoxy group, a s-butoxy group, an i-butoxy group and a t-butoxy group; and C1-6 haloalkoxy groups such as a 2-chloro-n-propoxy group, a 2,3-dichlorobutoxy group and a trifluoromethoxy group may be preferably exemplified, and C1-6 alkyl groups are more preferable.

As the "substituted or unsubstituted aminocarbonyl group" represented by $X^{1'}$, the same group as exemplified for $R^a$ and $R^b$ above is exemplified.

The "substituted or unsubstituted hydrazinyl group" represented by $X^{1'}$ is a group represented by the formula (a).

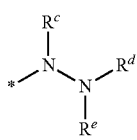 (a)

In the formula (a), * represents a binding position, $R^c$, $R^d$ and $R^e$ each independently represent a hydrogen atom, a C1-6 alkyl group or a substituted or unsubstituted phenylsulfonyl group.

As the "C1-6 alkyl group" represented by each of $R^c$, $R^d$ and $R^e$, the same group as exemplified for X above is exemplified.

As the "substituted phenylsulfonyl group" represented by each of $R^c$, $R^d$ and $R^e$, a paratoluenesulfonyl group or the like may be exemplified.

$X^{1'}$ is preferably a hydrogen atom, a C2-6 alkenyl group, a substituted or unsubstituted C3-8 cycloalkyl group, a substituted or unsubstituted phenyl group or a substituted or unsubstituted 5- to 6-membered heteroaryl group.

[$X^{2'}$]

In the formula (II), $X^{2'}$ represents a hydrogen atom, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C1-6 alkoxycarbonyl group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- to 6-membered heteroaryl group, a substituted or unsubstituted C6-10 aryloxy group, a substituted or unsubstituted 5- to 6-membered heteroaryloxy group, a substituted or unsubstituted amino group, a substituted or unsubstituted aminocarbonyl group, a substituted or unsubstituted hydrazinyl group, a nitro group, a cyano group or a halogeno group.

As the "substituted or unsubstituted C1-6 alkyl group" and the "halogeno group" represented by $X^{2'}$, the same groups as exemplified for $R^{2'}$ above are exemplified.

As the "substituted or unsubstituted C1-6 alkylsulfonyl group" represented by $X^{2'}$, the same group as exemplified for $R^{1'}$ above is exemplified.

As the "substituted or unsubstituted C6-10 aryl group" and the "substituted or unsubstituted 5- to 6-membered heteroaryl group" represented by $X^{2'}$, the same groups as exemplified for R above are exemplified.

As the "substituted or unsubstituted aminocarbonyl group" represented by $X^{2'}$, the same group as exemplified for $R^a$ and $R^b$ is exemplified.

As the "substituted or unsubstituted C2-6 alkenyl group", the "substituted or unsubstituted C2-6 alkynyl group", the "substituted or unsubstituted C1-6 alkoxy group", the "substituted or unsubstituted C1-6 alkoxycarbonyl group", the "substituted or unsubstituted C1-6 alkylthio group", the "substituted or unsubstituted C1-6 alkylsulfinyl group", the "substituted or unsubstituted C3-8 cycloalkyl group", the "substituted or unsubstituted C6-10 aryloxy group", the "substituted or unsubstituted 5- to 6-membered heteroaryloxy group", the "substituted or unsubstituted amino group" and the "substituted or unsubstituted hydrazinyl group" represented by $X^{2'}$, the same groups as exemplified for $X^{1'}$ above are exemplified.

$X^{2'}$ is preferably a hydrogen atom, a substituted or unsubstituted C1-6 alkoxy group, a substituted or unsubstituted C1-6 alkylsulfonyl group, a substituted or unsubstituted 5- to 6-membered heteroaryl group, a substituted or unsubstituted amino group or a halogeno group, more preferably a hydrogen atom or a substituted or unsubstituted 5- to 6-membered heteroaryl group.

It is to be noted that both $X^{1'}$ and $X^{2'}$ are not hydrogen atoms at the same time.

The heteroaryl azole compound of the present invention is excellent in control effect on pests such as various agricultural insect pests and mites affecting the growth of plants.

Also, the heteroaryl azole compound of the present invention is a highly safe substance because of less phytotoxicity to crops and low toxicity to fishes and warm-blooded animals. Hence, the heteroaryl azole compound of the present invention is useful as an active ingredient for insecticides or acaricides.

Furthermore, in recent years, many insect pests such as diamondback moth, white-backed plant hopper, leafhopper, and aphid have developed resistance to various existing chemicals, causing problems of insufficient efficacy of these chemicals. Thus, chemicals effective for insect pests of resistant strains have been desired. The heteroaryl azole compound of the present invention exhibits an excellent control effect not only on sensitive strains but also on insect pests of various resistant strains and even mites of acaricide-resistant strains.

The heteroaryl azole compound of the present invention is excellent in control effect on ectoparasites and endoparasites harmful to humans and animals. Also, the heteroaryl azole compound of the present invention is a highly safe substance because of low toxicity to fishes and warm-blooded animals. Hence, the heteroaryl azole compound of the present invention is useful as an active ingredient for ectoparasite and endoparasite control agents.

The heteroaryl azole compound of the present invention exhibits efficacy at every developmental stage of organisms to be controlled, and exhibits an excellent control effect on, for example, eggs, nymphs, larvae, pupae, and adults of mites, insects, and the like.

[Pest Control Agent]

The pest control agent of the present invention contains at least one active ingredient selected from the heteroaryl azole compounds of the present invention. The amount of the heteroaryl azole compound contained in the pest control agent of the present invention is not particularly limited as long as its pest control effect is exhibited. The pest control agent is an agent controlling pests and includes an insecticide or acaricide, an ectoparasite control agent, or an endoparasite control agent or expellant, or the like.

[Insecticide or Acaricide]

The insecticide or acaricide of the present invention contains at least one active ingredient selected from the heteroaryl azole compounds of the present invention. The amount of the heteroaryl azole compound contained in the insecticide or acaricide of the present invention is not particularly limited as long as its insecticidal or miticidal effect is exhibited.

The pest control agent or the insecticide or acaricide of the present invention is preferably used for plants such as cereals; vegetables; root vegetables; tubers and roots; flowers and ornamental plants; fruit trees; ornamental foliage plants and trees of tea, coffee, cacao, and the like; feed crops; lawn grasses; and cotton.

In the application to plants, the pest control agent or the insecticide or acaricide of the present invention may be used for any site such as a leaf, a stem, a stalk, a flower, a bud, a fruit, a seed, a sprout, a root, a tuber, a tuberous root, a shoot, or a slip.

The pest control agent or the insecticide or acaricide of the present invention is not particularly limited by the species of the plant to which the pest control agent or the insecticide or acaricide is applied. As the plant species, for example, an original species, a variant species, an improved variety, a cultivar, a mutant, a hybrid, a genetically modified organism (GMO) or the like may be exemplified.

The pest control agent of the present invention may be used in seed treatment, foliage application, soil application, submerged application, or the like in order to control various agricultural insect pests and mites.

Specific examples of various agricultural insect pests and mites controllable with the pest control agent of the present invention will be shown below.

(1) Butterflies or moths of the order Lepidoptera
- (a) moths of the family Arctiidae, for example, *Hyphantria cunea* and *Lemyra imparilis*;
- (b) moths of the family Bucculatricidae, for example, *Bucculatrix pyrivorella*;
- (c) moths of the family Carposinidae, for example, *Carposina sasakii*;
- (d) moths of the family Crambidae, for example, *Diaphania indica* and *Diaphania nitidalis* of *Diaphania* spp.; for example, *Ostrinia furnacalis*, *Ostrinia nubilalis*, and *Ostrinia scapulalis* of *Ostrinia* spp.; and *Chilo suppressalis*, *Cnaphalocrocis medinalis*, *Conogethes punctiferalis*, *Diatraea grandiosella*, *Glyphodes pyloalis*, *Hellula undalis*, and *Parapediasia teterrella*;
- (e) moths of the family Gelechiidae, for example, *Helcystogramma triannulella*, *Pectinophora gossypiella*, *Phthorimaea operculella*, and *Sitotroga cerealella*;
- (f) moths of the family Geometridae, for example, *Ascotis selenaria*;
- (g) moths of the family Gracillariidae, for example, *Caloptilia theivora*, *Phyllocnistis citrella*, and *Phyllonorycter ringoniella*;
- (h) butterflies of the family Hesperiidae, for example, *Parnara guttata*;
- (i) moths of the family Lasiocampidae, for example, *Malacosoma neustria*;
- (j) moths of the family Lymantriidae, for example, *Lymantria dispar* and *Lymantria monacha* of *Lymantria* spp.; and *Euproctis pseudoconspersa* and *Orgyia thyellina*;
- (k) moths of the family Lyonetiidae, for example, *Lyonetia clerkella* and *Lyonetia prunifoliella malinella* of *Lyonetia* spp.;
- (l) moths of the family Noctuidae, for example, *Spodoptera depravata*, *Spodoptera eridania*, *Spodoptera exigua*, *Spodoptera frugiperda*, *Spodoptera littoralis*, and *Spodoptera litura* of *Spodoptera* spp.; for example, *Autographa gamma* and *Autographa nigrisigna* of *Autographa* spp.; for example, *Agrotis ipsilon* and *Agrotis segetum* of *Agrotis* spp.; for example, *Helicoverpa armigera*, *Helicoverpa assulta*, and *Helicoverpa zea* of *Helicoverpa* spp.; for example, *Heliothis armigera* and *Heliothis virescens* of *Heliothis* spp.; and *Aedia leucomelas*, *Ctenoplusia agnata*, *Eudocima tyrannus*, *Mamestra brassicae*, *Mythimna separata*, *Naranga aenescens*, *Panolis japonica*, *Peridroma saucia*, *Pseudoplusia includens*, and *Trichoplusia ni*;
- (m) moths of the family Nolidae, for example, *Earias insulana*;
- (n) butterflies of the family Pieridae, for example, *Pieris brassicae* and *Pieris rapae crucivora* of *Pieris* spp.;
- (o) moths of the family Plutellidae, for example, *Acrolepiopsis sapporensis* and *Acrolepiopsis suzukiella* of *Acrolepiopsis* spp.; and *Plutella xylostella*;
- (p) moths of the family Pyralidae, for example, *Cadra cautella*, *Elasmopalpus lignosellus*, *Etiella zinckenella*, and *Galleria mellonella*;
- (q) moths of the family Sphingidae, for example, *Manduca quinquemaculata* and *Manduca sexta* of *Manduca* spp.;
- (r) moths of the family Stathmopodidae, for example, *Stathmopoda masinissa*;
- (s) moths of the family Tineidae, for example, *Tinea translucens*;
- (t) moths of the family Tortricidae, for example, *Adoxophyes honmai* and *Adoxophyes orana* of *Adoxophyes* spp.; for example, *Archips breviplicanus* and *Archips fuscocupreanus* of *Archips* spp.; and *Choristoneura fumiferana*, *Cydia pomonella*, *Eupoecilia ambiguella*, *Grapholitha molesta*, *Homona magnanima*, *Leguminivora glycinivorella*, *Lobesia botrana*, *Matsumuraeses phaseoli*, *Pandemis heparana*, and *Sparganothis pilleriana*;
- (u) moths of the family Yponomeutidae, for example, *Argyresthia conjugella*.

(2) Insect pests of the order Thysanoptera
- (a) insect pests of the family Phlaeothripidae, for example, *Ponticulothrips diospyrosi*;
- (b) insect pests of the family Thripidae, for example, *Frankliniella intonsa* and *Frankliniella occidentalis* of *Frankliniella* spp.; for example, *Thrips palmi* and *Thrips tabaci* of *Thrips* spp.; and *Heliothrips haemorrhoidalis* and *Scirtothrips dorsalis*.

(3) Insect pests of the order Hemiptera (A) the suborder Archaeorrhyncha
- (a) insect pests of the family Delphacidae, for example, *Laodelphax striatella*, *Nilaparvata lugens*, *Perkinsiella saccharicida*, and *Sogatella furcifera*.

(B) the suborder Clypeorrhyncha
- (a) insect pests of the family Cicadellidae, for example, *Empoasca fabae*, *Empoasca nipponica*, *Empoasca onukii*, and *Empoasca sakaii* of *Empoasca* spp.; and *Arboridia apicalis*, *Balclutha saltuella*, *Epiacanthus stramineus*, *Macrosteles striifrons*, and *Nephotettix cinctinceps*.

(C) the suborder Heteroptera
- (a) insect pests of the family Alydidae, for example, *Riptortus clavatus*;
- (b) insect pests of the family Coreidae, for example, *Cletus punctiger* and *Leptocorisa chinensis*;
- (c) insect pests of the family Lygaeidae, for example, *Blissus leucopterus*, *Cavelerius saccharivorus*, and *Togo hemipterus*;

(d) insect pests of the family Miridae, for example, *Halticus insularis, Lygus lineolaris, Psuedatomoscelis seriatus, Stenodema sibiricum, Stenotus rubrovittatus,* and *Trigonotylus caelestialium;*
(e) insect pests of the family Pentatomidae, for example, *Nezara antennata* and *Nezara viridula* of *Nezara* spp.; for example, *Eysarcoris aeneus, Eysarcoris lewisi,* and *Eysarcoris ventralis* of *Eysarcoris* spp.; and *Dolycoris baccarum, Eurydema rugosum, Glaucias subpunctatus, Halyomorpha halys, Piezodorus hybneri, Plautia crossota,* and *Scotinophora lurida;*
(f) insect pests of the family Pyrrhocoridae, for example, *Dysdercus cingulatus;*
(g) insect pests of the family Rhopalidae, for example, *Rhopalus msculatus;*
(h) insect pests of the family Scutelleridae, for example, *Eurygaster integriceps;*
(i) insect pests of the family Tingidae, for example, *Stephanitis nashi.*
(D) the suborder Sternorrhyncha
(a) insect pests of the family Adelgidae, for example, *Adelges laricis;*
(b) insect pests of the family Aleyrodidae, for example, *Bemisia argentifolii* and *Bemisia tabaci* of *Bemisia* spp.; and *Aleurocanthus spiniferus, Dialeurodes citri,* and *Trialeurodes vaporariorum;*
(c) insect pests of the family Aphididae, for example, *Aphis craccivora, Aphis fabae, Aphis forbesi, Aphis gossypii, Aphis pomi, Aphis sambuci,* and *Aphis spiraecola* of *Aphis* spp.; for example, *Rhopalosiphum maidis* and *Rhopalosiphum padi* of *Rhopalosiphum* spp.; for example, *Dysaphis plantaginea* and *Dysaphis radicola* of *Dysaphis* spp.; for example, *Macrosiphum avenae* and *Macrosiphum euphorbiae* of *Macrosiphum* spp.; for example, *Myzus cerasi, Myzus persicae,* and *Myzus varians* of *Myzus* spp.; and *Acyrthosiphon pisum, Aulacorthum solani, Brachycaudus helichrysi, Brevicoryne brassicae, Chaetosiphon fragaefolii, Hyalopterus pruni, Hyperomyzus lactucae, Lipaphis erysimi, Megoura viciae, Metopolophium dirhodum, Nasonovia ribis-nigri, Phorodon humuli, Schizaphis graminum, Sitobion avenae,* and *Toxoptera aurantii;*
(d) insect pests of the family Coccidae, for example, *Ceroplastes ceriferus* and *Ceroplastes rubens* of *Ceroplastes* spp.;
(e) insect pests of the family Diaspididae, *Pseudaulacaspis pentagona* and *Pseudaulacaspis prunicola* of *Pseudaulacaspis* spp.; for example, *Unaspis euonymi* and *Unaspis yanonensis* of *Unaspis* spp.; and *Aonidiella aurantii, Comstockaspis perniciosa, Fiorinia theae,* and *Pseudaonidia paeoniae;*
(f) insect pests of the family Margarodidae, for example, *Drosicha corpulenta* and *Icerya purchasi;*
(g) insect pests of the family Phylloxeridae, for example, *Viteus vitifolii;*
(h) insect pests of the family Pseudococcidae, for example, *Planococcus citri* and *Planococcus kuraunhiae* of *Planococcus* spp.; and *Phenacoccus solani* and *Pseudococcus comstocki;*
(i) insect pests of the family Psyllidae, for example, *Psylla mali* and *Psylla pyrisuga* of *Psylla* spp.; and *Diaphorina citri.*
(4) Insect pests of the suborder Polyphaga
(a) insect pests of the family Anobiidae, for example, *Lasioderma serricorne;*
(b) insect pests of the family Attelabidae, for example, *Byctiscus betulae* and *Rhynchites heros;*
(c) insect pests of the family Bostrichidae, for example, *Lyctus brunneus;*
(d) insect pests of the family Brentidae, for example, *Cylas formicarius;*
(e) insect pests of the family Buprestidae, for example, *Agrilus sinuatus;*
(f) insect pests of the family Cerambycidae, for example, *Anoplophora malasiaca, Monochamus alternatus, Psacothea hilaris,* and *Xylotrechus pyrrhoderus;*
(g) insect pests of the family Chrysomelidae, for example, *Bruchus pisorum* and *Bruchus rufimanus* of *Bruchus* spp.; for example, *Diabrotica barberi, Diabrotica undecimpunctata,* and *Diabrotica virgifera* of *Diabrotica* spp.; for example, *Phyllotreta nemorum* and *Phyllotreta striolata* of *Phyllotreta* spp.; and *Aulacophora femoralis, Callosobruchus chinensis, Cassida nebulosa, Chaetocnema concinna, Leptinotarsa decemlineata, Oulema oryzae,* and *Psylliodes angusticollis;*
(h) insect pests of the family Coccinellidae, for example, *Epilachna varivestis* and *Epilachna vigintioctopunctata* of *Epilachna* spp.;
(i) insect pests of the family Curculionidae, for example, *Anthonomus grandis* and *Anthonomus pomorum* of *Anthonomus* spp.; for example, *Sitophilus granarius* and *Sitophilus zeamais* of *Sitophilus* spp.; and *Echinocnemus squameus, Euscepes postfasciatus, Hylobius abietis, Hypera postica, Lissohoptrus oryzophilus, Otiorhynchus sulcatus, Sitona lineatus,* and *Sphenophorus venatus;*
(j) insect pests of the family Elateridae, for example, *Melanotus fortnumi* and *Melanotus tamsuyensis* of *Melanotus* spp.;
(k) insect pests of the family Nitidulidae, for example, *Epuraea domina;*
(l) insect pests of the family Scarabaeidae, for example, *Anomala cuprea* and *Anomala rufocuprea* of *Anomala* spp.; and *Cetonia aurata, Gametis jucunda, Heptophylla picea, Melolontha melolontha,* and *Popillia japonica;*
(m) insect pests of the family Scolytidae, for example, *Ips typographus;*
(n) insect pests of the family Staphylinidae, for example, *Paederus fuscipes;*
(o) insect pests of the family Tenebrionidae, for example, *Tenebrio molitor* and *Tribolium castaneum;*
(p) insect pests of the family Trogossitidae, for example, *Tenebroides mauritanicus.*
(5) Insect pests of the order Diptera
(A) the suborder Brachycera
(a) insect pests of the family Agromyzidae, for example, *Liriomyza bryoniae, Liriomyza chinensis, Liriomyza sativae,* and *Liriomyza trifolii* of *Liriomyza* spp.; and *Chromatomyia horticola* and *Agromyza oryzae;*
(b) insect pests of the family Anthomyiidae, for example, *Delia platura* and *Delia radicum* of *Delia* spp.; and *Pegomya cunicularia;*
(c) insect pests of the family Drosophilidae, for example, *Drosophila melanogaster* and *Drosophila suzukii* of *Drosophila* spp.;
(d) insect pests of the family Ephydridae, for example, *Hydrellia griseola;*
(e) insect pests of the family Psilidae, for example, *Psila rosae;*
(f) insect pests of the family Tephritidae, for example, *Bactrocera cucurbitae* and *Bactrocera dorsalis* of *Bac-* trocera spp.; for example, *Rhagoletis cerasi* and *Rhagoletis pomonella* of *Rhagoletis* spp.; and *Ceratitis capitata* and *Dacus oleae.*

(B) the suborder Nematocera (a) insect pests of the family Cecidomyiidae, for example, *Asphondylia yushimai, Contarinia sorghicola, Mayetiola destructor,* and *Sitodiplosis mosellana.*

(6) Insect pests of the order Orthoptera (a) insect pests of the family Acrididae, for example, *Schistocerca americana* and *Schistocerca gregaria* of *Schistocerca* spp.; and *Chortoicetes terminifera, Dociostaurus maroccanus, Locusta migratoria, Locustana pardalina, Nomadacris septemfasciata,* and *Oxya yezoensis;*

(b) insect pests of the family Gryllidae, for example, *Acheta domestica* and *Teleogryllus emma;*

(c) insect pests of the family Gryllotalpidae, for example, *Gryllotalpa orientalis;*

(d) insect pests of the family Tettigoniidae, for example, *Tachycines asynamorus.*

(7) Acari (A) Acaridida of the order Astigmata (a) mites of the family Acaridae, for example, *Rhizoglyphus echinopus* and *Rhizoglyphus robini* of *Rhizoglyphus* spp.; for example, *Tyrophagus neiswanderi, Tyrophagus perniciosus, Tyrophagus putrescentiae,* and *Tyrophagus similis* of *Tyrophagus* spp.; and *Acarus siro, Aleuroglyphus ovatus,* and *Mycetoglyphus fungivorus;*

(B) Actinedida of the order Prostigmata (a) mites of the family Tetranychidae, for example, *Bryobia praetiosa* and *Bryobia rubrioculus* of *Bryobia* spp.; for example, *Eotetranychus asiaticus, Eotetranychus boreus, Eotetranychus celtis, Eotetranychus geniculatus, Eotetranychus kankitus, Eotetranychus pruni, Eotetranychus shii, Eotetranychus smithi, Eotetranychus suginamensis,* and *Eotetranychus uncatus* of *Eotetranychus* spp.; for example, *Oligonychus hondoensis, Oligonychus ilicis, Oligonychus karamatus, Oligonychus mangiferus, Oligonychus orthius, Oligonychus perseae, Oligonychus pustulosus, Oligonychus shinkajii,* and *Oligonychus ununguis* of *Oligonychus* spp.; for example, *Panonychus citri, Panonychus mori,* and *Panonychus ulmi* of *Panonychus* spp.; for example, *Tetranychus cinnabarinus, Tetranychus kanzawai, Tetranychus ludeni, Tetranychus quercivorus, Tetranychus phaselus, Tetranychus urticae, Tetranychus viennensis,* and *Tetranychus evansi* of *Tetranychus* spp.; for example, *Aponychus corpuzae* and *Aponychus firmianae* of *Aponychus* spp.; for example, *Sasanychus akitanus* and *Sasanychus pusillus* of *Sasanychus* spp.; for example, *Schizotetranychus celarius, Schizotetranychus longus, Schizotetranychus miscanthi, Schizotetranychus recki,* and *Schizotetranychus schizopus* of *Schizotetranychus* spp.; and *Tetranychina harti, Tuckerella pavoniformis,* and *Yezonychus sapporensis;*

(b) mites of the family Tenuipalpidae, for example, *Brevipalpus lewisi, Brevipalpus obovatus, Brevipalpus phoenicis, Brevipalpus russulus,* and *Brevipalpus californicus* of *Brevipalpus* spp.; for example, *Tenuipalpus pacificus* and *Tenuipalpus zhizhilashviliae* of *Tenuipalpus* spp.; and *Dolichotetranychus floridanus;*

(c) mites of the family Eriophyidae, for example, *Aceria diospyri, Aceria ficus, Aceria japonica, Aceria kuko, Aceria paradianthi, Aceria tiyingi, Aceria tulipae,* and *Aceria zoysiea* of *Aceria* spp.; for example, *Eriophyes chibaensis* and *Eriophyes emarginatae* of *Eriophyes* spp.; for example, *Aculops lycopersici* and *Aculops pelekassi* of *Aculops* spp.; for example, *Aculus fockeui* and *Aculus schlechtendali* of *Aculus* spp.; and *Acaphylla theavagrans, Calacarus carinatus, Colomerus vitis, Calepitrimerus vitis, Epitrimerus pyri, Paraphytoptus kikus, Paracalacarus podocarpi,* and *Phyllocotruta citri;*

(d) mites of the family Tarsonemidae, for example, *Tarsonemus bilobatus* and *Tarsonemus waitei* of *Tarsonemus* spp.; and *Phytonemus pallidus* and *Polyphagotarsonemus latus;*

(e) mites of the family Penthaleidae, for example, *Penthaleus erythrocephalus* and *Penthaleus major* of *Penthaleus* spp.

The pest control agent of the present invention may be used as a mixture or in combination with another active ingredient such as a fungicide, an insecticide or acaricide, a nematicide, or a pesticide for soil insect pests; a plant regulating agent, a synergist, a fertilizer, a soil improvement agent, animal feed, or the like.

The combination of the heteroaryl azole compound of the present invention with another active ingredient may be expected to have synergistic effects on insecticidal, miticidal, or nematicidal activity. The synergistic effects may be confirmed by the equation of Colby (Colby. S. R.; Calculating Synergistic and Antagonistic Responses of Herbicide Combinations; Weeds 15, p. 20-22, 1967) according to a standard method.

Specific examples of the insecticide or acaricide, the nematicide, the pesticide for soil insect pests, the anthelmintic agent, and the like that may be used as a mixture or in combination with the pest control agent of the present invention will be shown below.

(1) Acetylcholinesterase inhibitors:

(a) carbamate-based: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylylcarb, fenothiocarb, MIPC, MPMC, MTMC, aldoxycarb, allyxycarb, aminocarb, bufencarb, cloethocarb, metam sodium, and promecarb;

(b) organophosphorus-based: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion, bromophos-ethyl, BRP, carbophenothion, cyanofenphos, CYAP, demeton-S-methyl sulfone, dialifos, dichlofenthion, dioxabenzofos, etrimfos, fensulfothion, flupyrazofos, fonofos, formothion, fosmethilan, isazofos, iodofenphos, methacrifos, pirimiphos-ethyl, phosphocarb, propaphos, prothoate, and sulprofos.

(2) GABAergic chloride ion channel antagonists: acetoprole, chlordene, endosulfan, ethiprole, fipronil, pyrafluprole, pyriprole, camphechlor, heptachlor, and dienochlor.

(3) Sodium channel modulators: acrinathrin, d-cis-trans allethrin, d-trans allethrin, bifenthrin, bioallethrin, bioallethrin s-cyclopentyl isomer, bioresmethrin, cycloprothrin, cyfluthrin, β-cyfluthrin, cyhalothrin, λ-cyhalothrin, γ-cyhalothrin, cypermethrin, α-cypermethrin, β-cypermethrin, θ-cypermethrin, ζ-cypermethrin, cyphenothrin [(1R)-trans isomer], deltamethrin, empenthrin [(EZ)-(1R)-Isomer], esfenvalerate, etofenprox, fenpropathrin, fenvalerate, flucythrinate, flumethrin, τ-fluvalinate, halfenprox, imiprothrin, kadethrin, permethrin, phenothrin [(1R)-trans isomer], prallethrin, pyrethrum, resmethrin, silafluofen, tefluthrin, tetramethrin [(1R)-isomer], tralomethrin, transfluthrin, allethrin, pyrethrins, pyrethrin I, pyrethrin II, profluthrin, dimefluthrin, bioethanomethrin, biopermethrin, transpermethrin, fenfluthrin, fenpirithrin, flubrocythrinate, flufenprox, metofluthrin, protrifenbute, pyresmethrin, and terallethrin.

(4) Nicotinic acetylcholine receptor agonists: acetamiprid, clothianidin, dinotefuran, imidacloprid, nitenpyram, nithiazine, thiacloprid, thiamethoxam, sulfoxaflor, nicotine, flupyradifurone, and flupyrimine.

(5) Nicotinic acetylcholine receptor allosteric modulators: spinetoram and spinosad.

(6) Chloride channel activators: abamectin, emamectin-benzoate, lepimectin, milbemectin, ivermectin, selamectin, doramectin, eprinomectin, moxidectin, milbemycin, milbemycin oxime, and nemadectin.

(7) Juvenile hormone-like substances: hydroprene, kinoprene, methoprene, fenoxycarb, pyriproxyfen, diofenolan, epofenonane, and triprene.

(8) Other nonspecific inhibitors: methyl bromide, chloropicrin, sulfuryl fluoride, borax, and tartar emetic.

(9) Homoptera selective feeding inhibitors: flonicamid, pymetrozine, and pyrifluquinazon.

(10) Mite growth inhibitors: clofentezine, diflovidazin, hexythiazox, and etoxazole.

(11) Insect midgut inner membrane disrupting agents derived from microorganisms: *Bacillus thuringiensis* subsp. *Israelensis*, *Bacillus sphaericus*, *Bacillus thuringiensis* subsp. *aizawai*, *Bacillus thuringiensis* subsp. *kurstaki*, *Bacillus thuringiensis* subsp. *tenebrionis*, and Bt crop proteins: Cry1Ab, Cry1Ac, Cry1Fa, Cry1A.105, Cry2Ab, Vip3A, mCry3A, Cry3Ab, Cry3Bb, and Cry34Ab1/Cry35Ab1.

(12) Mitochondrial ATP biosynthetic enzyme inhibitors: diafenthiuron, azocyclotin, cyhexatin, fenbutatin oxide, propargite, and tetradifon.

(13) Oxidative phosphorylation uncouplers: chlorfenapyr, sulfluramid, DNOC, binapacryl, dinobuton, and dinocap.

(14) Nicotinic acetylcholine receptor channel blockers: bensultap, cartap hydrochloride, nereistoxin, thiosultap-sodium, and thiocyclam.

(15) Chitin synthesis inhibitors: bistrifluron, chlorfluazuron, diflubenzuron, flucycloxuron, flufenoxuron, hexaflumuron, lufenuron, novaluron, noviflumuron, teflubenzuron, triflumuron, buprofezin, and fluazuron.

(16) Diptera molting disrupting agents: cyromazine.

(17) Molting hormone receptor agonists: chromafenozide, halofenozide, methoxyfenozide, and tebufenozide.

(18) Octopamine receptor agonists: amitraz, demiditraz, and chlordimeform.

(19) Mitochondrial electron transport system complex III inhibitors: acequinocyl, fluacrypyrim, and hydramethylnon.

(20) Mitochondrial electron transport system complex I inhibitors: fenazaquin, fenpyroximate, pyrimidifen, pyridaben, tebufenpyrad, tolfenpyrad, and rotenone.

(21) Voltage-gated sodium channel blockers: indoxacarb and metaflumizone.

(22) Acetyl CoA carboxylase inhibitors: spirodiclofen, spiromesifen, and spirotetramat.

(23) Mitochondrial electron transport system complex IV inhibitors: aluminum phosphide, calcium phosphide, phosphine, zinc phosphide, and cyanide.

(24) Mitochondrial electron transport system complex II inhibitors: cyenopyrafen, cyflumetofen, and pyflubumide.

(25) Ryanodine receptor modulators: chlorantraniliprole, cyantraniliprole, flubendiamide, cyclaniliprole, and tetraniliprole.

(26) Mixed function oxidase inhibitor compounds: piperonyl butoxide.

(27) Latrophilin receptor agonists: depsipeptide, cyclodepsipeptide, 24 membered cyclodepsipeptide, and emodepside.

(28) Other agents (based on an unknown mechanism of action): azadirachtin, benzoximate, bifenazate, bromopropylate, quinomethionate, cryolite, dicofol, pyridalyl, benclothiaz, sulfur, amidoflumet, 1,3-dichloropropene, DCIP, phenisobromolate, benzomate, metaldehyde, chlorobenzilate, clothiazoben, dicyclanil, fenoxacrim, fentrifanil, flubenzimine, fluphenazine, gossyplure, japonilure, metoxadiazone, oil, potassium oleate, tetrasul, triarathene, afidopyropen, flometoquin, flufiprole, fluensulfone, meperfluthrin, tetramethylfluthrin, tralopyril, dimefluthrin, methylneodecanamide, fluralaner, afoxolaner, fluxametamide, 5-[5-(3,5-dichlorophenyl)-5-trifluoromethyl-4,5-dihydroisoxazole-3-yl]-2-(1H-1,2,4-triazole-1-yl)benzonitrile (CAS: 943137-49-3), broflanilide, other m-diamides, steinernema carpocapsae, steinernema glaseri, *Pasteuria penetrans*, *Paecilomyces tenuipes*, *Paecilomyces fumosoroseus*, *Beauveria bassiana*, *Beauveria brongniartii*, *Metarhizium anisopliae*, *Verticillium lecanii*, Acynonapyr benzpyrimoxan, oxazosulfyl, tyclopyrazoflor, and fluhexafon.

(29) Anthelmintic agents:
  (a) benzimidazole-based: fenbendazole, albendazole, triclabendazole, oxibendazole, mebendazole, oxfendazole, parbendazole, flubendazole, febantel, netobimin, thiophanate, thiabendazole, and cambendazole;
  (b) salicylanilide-based: closantel, oxyclozanide, rafoxanide, and niclosamide;
  (c) substituted phenol-based: nitroxinil and nitroscanate;
  (d) pyrimidine-based: pyrantel and morantel;
  (e) imidazothiazole-based: levamisole and tetramisole;
  (f) tetrahydropyrimidine-based: praziquantel and epsiprantel;
  (g) other anthelmintic agents: cyclodiene, ryania, clorsulon, metronidazole, demiditraz, piperazine, diethylcarbamazine, dichlorophen, monepantel, tribendimidine, amidantel, thiacetarsamide, melarsomine, and arsenamide.

Specific examples of the fungicide that may be used as a mixture or in combination with the pest control agent of the present invention will be shown below.

(1) Nucleic Acid Biosynthesis Inhibitors:
  (a) RNA polymerase I inhibitors: benalaxyl, benalaxyl-M, furalaxyl, metalaxyl, metalaxyl-M, oxadixyl, clozylacon, and ofurace;
  (b) adenosine deaminase inhibitors: bupirimate, dimethirimol, and ethirimol;
  (c) DNA/RNA synthesis inhibitors: hymexazol and octhilinone;

(d) DNA topoisomerase II inhibitors: oxolinic acid.
(2) Mitotic Inhibitors and Cell Division Inhibitors:
  (a) β-tubulin polymerization inhibitors: benomyl, carbendazim, chlorfenazole, fuberidazole, thiabendazole, thiophanate, thiophanate-methyl, diethofencarb, zoxamide, and ethaboxam;
  (b) cell division inhibitors: pencycuron;
  (c) spectrin-like protein delocalization inhibitors: fluopicolide.
(3) Respiration Inhibitors:
  (a) complex I NADH oxidation-reduction enzyme inhibitors: diflumetorim and tolfenpyrad;
  (b) complex II succinate dehydrogenase inhibitors: benodanil, flutolanil, mepronil, isofetamid, fluopyram, fenfuram, furmecyclox, carboxin, oxycarboxin, thifluzamide, benzovindiflupyr, bixafen, fluxapyroxad, furametpyr, isopyrazam, penflufen, penthiopyrad, sedaxane, boscalid, pyraziflumid, pydiflumetofen, isoflucypram, and inpyrfluxam;
  (c) complex III ubiquinol oxidase Qo inhibitors: azoxystrobin, coumoxystrobin, coumethoxystrobin, enoxastrobin, flufenoxystrobin, picoxystrobin, pyraoxystrobin, pyraclostrobin, pyrametostrobin, triclopyricarb, kresoxim-methyl, trifloxystrobin, dimoxystrobin, fenaminstrobin, metominostrobin, orysastrobin, famoxadone, fluoxastrobin, fenamidone, pyribencarb, mandestrobin and metyltetraprole;
  (d) complex III ubiquinol reductase Qi inhibitors: cyazofamid, amisulbrom, and fenpicoxamid;
  (e) oxidative phosphorylation uncoupling agents: binapacryl, meptyldinocap, dinocap, fluazinam, and ferimzone;
  (f) oxidative phosphorylation inhibitors (ATP synthase inhibitors): fentin acetate, fentin chloride, and fentin hydroxide;
  (g) ATP production inhibitors: silthiofam;
  (h) complex III: Qx (unknown) inhibitor of cytochrome bc1 (ubiquinone reductase): ametoctradin.
(4) Amino Acid and Protein Synthesis Inhibitors
  (a) methionine biosynthesis inhibitors: andoprim, cyprodinil, mepanipyrim, and pyrimethanil;
  (b) protein synthesis inhibitors: blasticidin-S, kasugamycin, kasugamycin hydrochloride, streptomycin, and oxytetracycline.
(5) Signal Transduction Inhibitors:
  (a) signal transduction inhibitors: quinoxyfen and proquinazid;
  (b) MAP/histidine kinase inhibitors in osmotic signal transduction: fenpiclonil, fludioxonil, chlozolinate, iprodione, procymidone, and vinclozolin.
(6) Lipid and Cell Membrane Synthesis Inhibitors:
  (a) phospholipid biosynthesis, methyltransferase inhibitors: edifenphos, iprobenfos, pyrazophos, and isoprothiolane;
  (b) lipid peroxidation agents: biphenyl, chloroneb, dichloran, quintozene, tecnazene, tolclofos-methyl, and etridiazole;
  (c) agents that act on cell membranes: iodocarb, propamocarb, propamocarb-hydrochloride, propamocarb-fosetylate, and prothiocarb;
  (d) microorganisms that disrupt cell membranes of pathogens: *Bacillus subtilis, Bacillus subtilis* strain QST713 strain, *Bacillus subtilis* FZB24, *Bacillus subtilis* strain MBI600, *Bacillus subtilis* strain D747, and *Bacillus amyloliquefaciens;*
  (e) agents that disrupt cell membranes: *melaleuca alternifolia* (tea tree) extract.
(7) Cell Membrane Sterol Biosynthesis Inhibitors:
  (a) C14-demethylation inhibitors in sterol biosynthesis: triforine, pyrifenox, pyrisoxazole, fenarimol, flurprimidol, nuarimol, imazalil, imazalil-sulfate, oxpoconazole fumarate, pefurazoate, prochloraz, triflumizole, viniconazole, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, fluquinconazole, simeconazole, tebuconazole, tetraconazole, triadimefon, triadimenol, triticonazole, prothioconazole, voriconazole and mefentrifluconazole;
  (b) Δ14 reductase and sterol Δ8→Δ7-isomerase inhibitors in sterol biosynthesis: aldimorph, dodemorph, dodemorph acetate, fenpropimorph, tridemorph, fenpropidin, piperalin, and spiroxamine;
  (c) 3-keto reductase inhibitors in C4-demethylation in the sterol biosynthesis system: fenhexamid and fenpyrazamine;
  (d) squalene epoxidase inhibitors in the sterol biosynthesis system: pyributicarb, naftifine, and terbinafine.
(8) Cell Wall Synthesis Inhibitors
  (a) trehalase inhibitors: validamycin;
  (b) chitin synthase inhibitors: polyoxins and polyoxorim;
  (c) cellulose synthase inhibitors: dimethomorph, flumorph, pyrimorph, benthiavalicarb-isopropyl, iprovalicarb, valifenalate, and mandipropamid.
(9) Melanin Biosynthesis Inhibitors
  (a) melanin biosynthesis reductase inhibitors: fthalide, pyroquilon, and tricyclazole;
  (b) melanin biosynthesis anhydrase inhibitors: carpropamid, diclocymet, and fenoxanil;
  (c) melanin biosynthesis polyketide synthesis inhibitors: tolprocarb.
(10) Host Plant Resistance Inducers:
  (a) agents that act on salicylic acid synthesis pathway: acibenzolar-S-methyl;
  (b) others: probenazole, tiadinil, isotianil, dichlobentiazox, laminarin, and *Reynoutria sachalinensis* extract.
(11) Agents with unknown mode of action: cymoxanil, fosetyl-aluminum, phosphoric acid (phosphate), tecloftalam, triazoxide, flusulfamide, diclomezine, methasulfocarb, cyflufenamid, metrafenone, pyriofenone, dodine, dodine free base, and flutianil.
(12) Agents having multiple active sites: copper (copper salt), bordeaux mixture, copper hydroxide, copper naphthalate, copper oxide, copper oxychloride, copper sulfate, sulfur, sulfur products, calcium polysulfide, ferbam, mancozeb, maneb, mancopper, metiram, polycarbamate, propineb, thiram, zineb, ziram, captan, captafol, folpet, chlorothalonil, dichlofluanid, tolylfluanid, guazatine, iminoctadine triacetate, iminoctadine trialbesilate, anilazine, dithianon, quinomethionate, and fluoroimide.
(13) Other agents: DBEDC, fluorofolpet, guazatine acetate, bis(8-quinolinolato)copper (II), propamidine, chloropicrin, cyprofuram, *Agrobacterium*, bethoxazin, diphenylamine, methyl isothiocyanate (MITC), mildiomycin, capsaicin, cufraneb, cyprosulfamide, dazomet, debacarb, dichlorophen, flumetover, fosetyl-calcium, fosetyl-sodium, irumamycin, natamycin, nitrothal isopropyl, oxamocarb, pyrrolnitrin, tebufloquin, tolnifanide, zarilamide, algophase, amicarthiazol, oxathiapiprolin, metiram zinc, benthiazole, trichlamide, uniconazole, oxyfenthiin, picarbutrazox, dichlobentiazox, quinofumelin, thiuram, ambam, *Agrobac-*

*terium radiobacter, Coniothyrium minitans, Pseudomonas fluorescens, Pseudomonas rhodesiae, Talaromyces flavus, Trichoderma atroviride, Erwinia carotovora* subsp. *carotovora, Bacillus simplex, Variovorax paradoxus, Lactobacillus plantarum*, florylpicoxamid, pyrapropoyne, fluindapyr, aminopyrifen, pyridachlometyl, and ipflufenoquin.

Specific examples of the plant regulating agent that may be used as a mixture or in combination with the pest control agent of the present invention will be shown below.

Abscisic acid, kinetin, benzylaminopurine, 1,3-diphenylurea, forchlorfenuron, thidiazuron, chlorfenuron, dihydrozeatin, gibberellin A, gibberellin A4, gibberellin A7, gibberellin A3, 1-methylcyclopropane, N-acetyl aminoethoxyvinyl glycine (also called aviglycine), aminooxyacetate, silver nitrate, cobalt chloride, IAA, 4-CPA, cloprop, 2,4-D, MCPB, indole-3-butyrate, dichlorprop, phenothiol, 1-naphthyl acetamide, ethychlozate, cloxyfonac, maleic acid hydrazide, 2,3,5-triiodobenzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenylethyl)aminobutyric acid, ethephon, chlormequat, mepiquat chloride, benzyladenine, 5-amino levulinic acid, and daminozide.

[Ectoparasite Control Agent]

The ectoparasite control agent of the present invention contains at least one active ingredient selected from the heteroaryl azole compounds of the present invention. The amount of the heteroaryl azole compound contained in the ectoparasite control agent of the present invention is not particularly limited as long as its ectoparasite control effect is exhibited.

As the host animal to be treated with the ectoparasite control agent of the present invention, a warm-blooded animal such as a human and a livestock mammal (e.g., a cow, a horse, a pig, sheep, and a goat), a laboratory animal (e.g., a mouse, a rat, and a sand rat), a pet animal (e.g., a hamster, a guinea pig, a dog, a cat, a squirrel, a rabbit, and a ferret), wild and zoo mammals (e.g., a monkey, a fox, a deer, and a buffalo), a fowl (e.g., a turkey, a duck, a chicken, a quail, and a goose), and a pet bird (e.g., a pigeon, a parrot, a myna bird, a Java sparrow, a parakeet, a Bengalese finch, and a canary bird); and fishes such as salmon, trout, and koi may be exemplified. In addition, a bee, a stag beetle and a beetle may be exemplified.

The ectoparasite control agent of the present invention may be applied by a known veterinary approach (local, oral, parenteral or subcutaneous administration). As the method therefor, a method of orally administering tablets, capsules, feed or the like containing the ectoparasite control agent to animals; a method of administering the ectoparasite control agent through dipping liquids, suppositories, injection (intramuscular, subcutaneous, intravenous, or intraperitoneal injection, etc.) or the like to animals; a method of locally administering oily or aqueous liquid formulations by spraying, pour-on, spot-on or the like; and a method of kneading the ectoparasite control agent into a resin, shaping the kneaded product into a suitable shape such as a collar or an ear tag, and attaching it to animals for local administration; or the like may be exemplified.

Ectoparasites parasitize the inside or the body surface of host animals, particularly, warm-blooded animals. Specifically, the ectoparasites parasitize the backs, armpits, lower abdomens, inner thighs, or the like of host animals and live by obtaining nutrients such as blood or dandruff from the animals. As the ectoparasite, mites, lice, fleas, a mosquito, a stable fly, a flesh fly or the like may be exemplified. Specific examples of the ectoparasite controllable with the ectoparasite control agent of the present invention will be shown below.

(1) Acari mites of the family Dermanyssidae, mites of the family Macronyssidae, mites of the family Laelapidae, mites of the family Varroidae, mites of the family Argasidae, mites of the family Ixodidae, mites of the family Psoroptidae, mites of the family Sarcoptidae, mites of the family Knemidokoptidae, mites of the family Demodixidae, mites of the family Trombiculidae, and insect parasitic mites such as mites of the family Canestriniidae.

(2) The order Phthiraptera lice of the family Haematopinidae, lice of the family Linognathidae, bird lice of the family Menoponidae, bird lice of the family Philopteridae, and bird lice of the family Trichodectidae.

(3) The order Siphonaptera fleas of the family Pulicidae, for example, *Ctenocephalides canis* and *Ctenocephalides felis* of *Ctenocephalides* spp.;

fleas of the family Tungidae, fleas of the family Ceratophyllidae, and fleas of the family Leptopsyllidae.

(4) The order Hemiptera (5) Insect pests of the order Diptera mosquitos of the family Culicidae, black flies of the family Simuliidae, biting midges of the family Ceratopogonidae, horseflies of the family Tabanidae, flies of the family Muscidae, tsetse flies of the family Glossinidae, flesh flies of the family Sarcophagidae, flies of the family Hippoboscidae, flies of the family Calliphoridae, and flies of the family Oestridae.

[Endoparasite Control Agent or Expellant]

The endoparasite control agent or expellant of the present invention contains at least one active ingredient selected from the heteroaryl azole compounds of the present invention. The amount of the heteroaryl azole compound contained in the endoparasite control agent or expellant of the present invention is not particularly limited as long as its endoparasite control effect is exhibited.

The parasite targeted by the endoparasite control agent or expellant of the present invention parasitizes the inside of host animals, particularly, warm-blooded animals or fishes (endoparasite). As the host animal for which the endoparasite control agent or expellant of the present invention is effective, a warm-blooded animal such as a human and a livestock mammal (e.g., a cow, a horse, a pig, sheep, and a goat), a laboratory animal (e.g., a mouse, a rat, and a sand rat), a pet animal (e.g., a hamster, a guinea pig, a dog, a cat, a squirrel, a rabbit, and a ferret), wild and zoo mammals (e.g., a monkey, a fox, a deer, and a buffalo), a fowl (e.g., a turkey, a duck, a chicken, a quail, and a goose), and a pet bird (e.g., a pigeon, a parrot, a myna bird, a Java sparrow, a parakeet, a Bengalese finch, and a canary bird); and fishes such as salmon, trout, and koi may be exemplified. Parasitic diseases mediated by parasites may be prevented or treated by controlling and expelling the parasites.

As the parasite to be controlled or expelled, the following may be exemplified.

(1) Nematodes of the order Dioctophymatida
  (a) kidney worms of the family Dioctophymatidae, for example, *Dioctophyma renale* of *Dioctophyma* spp.;
  (b) kidney worms of the family Soboliphymatidae, for example, *Soboliphyme abei* and *Soboliphyme baturini* of *Soboliphyme* spp.

(2) Nematodes of the order Trichocephalida
(a) trichinae of the family Trichinellidae, for example, *Trichinella spiralis* of *Trichinella* spp.;
(b) whipworms of the family Trichuridae, for example, *Capillaria annulata*, *Capillaria contorta*, *Capillaria hepatica*, *Capillaria perforans*, *Capillaria plica*, and *Capillaria suis* of *Capillaria* spp.; and *Trichuris vulpis*, *Trichuris discolor*, *Trichuris ovis*, *Trichuris skrjabini*, and *Trichuris suis* of *Trichuris* spp.

(3) Nematodes of the order Rhabditida
threadworms of the family Strongyloididae, for example, *Strongyloides papillosus*, *Strongyloides planiceps*, *Strongyloides ransomi*, *Strongyloides suis*, *Strongyloides stercoralis*, *Strongyloides tumefaciens*, and *Strongyloides ratti* of *Strongyloides* spp.

(4) Nematodes of the order Strongylida
hookworms of the family Ancylostomatidae, for example, *Ancylostoma braziliense*, *Ancylostoma caninum*, *Ancylostoma duodenale*, and *Ancylostoma tubaeforme* of *Ancylostoma* spp.; *Uncinaria stenocephala* of *Uncinaria* spp.; and *Bunostomum phlebotomum* and *Bunostomum trigonocephalum* of *Bunostomum* spp.

(5) Nematodes of the order Strongylida
(a) nematodes of the family Angiostrongylidae, for example, *Aelurostrongylus abstrusus* of *Aelurostrongylus* spp.; and *Angiostrongylus vasorum* and *Angiostrongylus cantonesis* of *Angiostrongylus* spp.;
(b) nematodes of the family Crenosomatidae, for example, *Crenosoma aerophila* and *Crenosoma vulpis* of *Crenosoma* spp.;
(c) nematodes of the family Filaroididae, for example, *Filaroides hirthi* and *Filaroides osleri* of *Filaroides* spp.;
(d) lungworms of the family Metastrongylidae, for example, *Metastrongylus apri*, *Metastrongylus asymmetricus*, *Metastrongylus pudendotectus*, and *Metastrongylus salmi* of *Metastrongylus* spp.;
(e) gapeworms of the family Syngamidae, for example, *Cyathostoma bronchialis* of *Cyathostoma* spp.; and *Syngamus skrjabinomorpha* and *Syngamus trachea* of *Syngamus* spp.

(6) Nematodes of the order Strongylida
(a) nematodes of the family Molineidae, for example, *Nematodirus filicollis* and *Nematodirus spathiger* of *Nematodirus* spp.;
(b) nematodes of the family Dictyocaulidae, for example, *Dictyocaulus filaria* and *Dictyocaulus viviparus* of *Dictyocaulus* spp.;
(c) nematodes of the family Haemonchidae, for example, *Haemonchus contortus* of *Haemonchus* spp.; and *Mecistocirrus digitatus* of *Mecistocirrus* spp.;
(d) nematodes of the family Haemonchidae, for example, *Ostertagia ostertagi* of *Ostertagia* spp.;
(e) nematodes of the family Heligmonellidae, for example, *Nippostrongylus braziliensis* of *Nippostrongylus* spp.;
(f) nematodes of the family Trichostrongylidae, for example, *Trichostrongylus axei*, *Trichostrongylus colubriformis*, and *Trichostrongylus tenuis* of *Trichostrongylus* spp.; *Hyostrongylus rubidus* of *Hyostrongylus* spp.; and *Obeliscoides cuniculi* of *Obeliscoides* spp.

(7) Nematodes of the order Strongylida
(a) nematodes of the family Chabertiidae, for example, *Chabertia ovina* of *Chabertia* spp.; and *Oesophagostomum brevicaudatum*, *Oesophagostomum columbianum*, *Oesophagostomum dentatum*, *Oesophagostomum georgianum*, *Oesophagostomum maplestonei*, *Oesophagostomum quadrispinulatum*, *Oesophagostomum radiatum*, *Oesophagostomum venulosum*, and *Oesophagostomum watanabei* of *Oesophagostomum* spp.;
(b) nematodes of the family Stephanuridae, for example, *Stephanurus dentatus* of *Stephanurus* spp.;
(c) nematodes of the family Strongylidae, for example, *Strongylus asini*, *Strongylus edentatus*, *Strongylus equinus*, and *Strongylus vulgaris* of *Strongylus* spp.

(8) Nematodes of the order Oxyurida
nematodes of the family Oxyuridae, for example, *Enterobius anthropopitheci* and *Enterobius vermicularis* of *Enterobius* spp.; *Oxyuris equi* of *Oxyuris* spp.; and *Passalurus ambiguous* of *Passalurus* spp.

(9) Nematodes of the order Ascaridida
(a) nematodes of the family Ascaridiidae, for example, *Ascaridia galli* of *Ascaridia* spp.;
(b) nematodes of the family Heterakidae, for example, *Heterakis beramporia*, *Heterakis brevispiculum*, *Heterakis gallinarum*, *Heterakis pusilla*, and *Heterakis putaustralis* of *Heterakis* spp.;
(c) nematodes of the family Anisakidae, for example, *Anisakis simplex* of *Anisakis* spp.;
(d) nematodes of the family Ascarididae, for example, *Ascaris lumbricoides* and *Ascaris suum* of *Ascaris* spp.; and *Parascaris equorum* of *Parascaris* spp.;
(e) nematodes of the family Toxocaridae, for example, *Toxocara canis*, *Toxocara leonina*, *Toxocara suum*, *Toxocara vitulorum*, and *Toxocara cati* of *Toxocara* spp.

(10) Nematodes of the order Spirurida
(a) nematodes of the family Onchocercidae, for example, *Brugia malayi*, *Brugia pahangi*, and *Brugia patei* of *Brugia* spp.; *Dipetalonema reconditum* of *Dipetalonema* spp.; *Dirofilaria immitis* of *Dirofilaria* spp.; *Filaria oculi* of *Filaria* spp.; and *Onchocerca cervicalis*, *Onchocerca gibsoni*, and *Onchocerca gutturosa* of *Onchocerca* spp.;
(b) nematodes of the family Setariidae, for example, *Setaria digitata*, *Setaria equina*, *Setaria labiatopapillosa*, and *Setaria marshalli* of *Setaria* spp.; and *Wuchereria bancrofti* of *Wuchereria* spp.;
(c) nematodes of the family Filariidae, for example, *Parafilaria multipapillosa* of *Parafilaria* spp.; and *Stephanofilaria assamensis*, *Stephanofilaria dedoesi*, *Stephanofilaria kaeli*, *Stephanofilaria okinawaensis*, and *Stephanofilaria stilesi* of *Stephanofilaria* spp.

(11) Nematodes of the order Spirurida
(a) nematodes of the family Gnathostomatidae, for example, *Gnathostoma doloresi* and *Gnathostoma spinigerum* of *Gnathostoma* spp.;
(b) nematodes of the family Habronematidae, for example, *Habronema majus*, *Habronema microstoma*, and *Habronema muscae* of *Habronema* spp.; and *Draschia megastoma* of *Draschia* spp.;
(c) nematodes of the family Physalopteridae, for example, *Physaloptera canis*, *Physaloptera cesticillata*, *Physaloptera erdocyona*, *Physaloptera felidis*, *Physaloptera gemina*, *Physaloptera papilloradiata*, *Physaloptera praeputialis*, *Physaloptera pseudopraerutialis*, *Physaloptera rara*, *Physaloptera sibirica*, and *Physaloptera vulpineus* of *Physaloptera* spp.;
(d) nematodes of the family Gongylonematidae, for example, *Gongylonema pulchrum* of *Gongylonema* spp.;

(e) nematodes of the family Spirocercidae, for example, *Ascarops strongylina* of *Ascarops* spp.;

(f) nematodes of the family Thelaziidae, for example, *Thelazia callipaeda, Thelazia gulosa, Thelazia lacrymalis, Thelazia rhodesi*, and *Thelazia skrjabini* of *Thelazia* spp.

[Control Agent for Other Pests]

The heteroaryl azole compound of the present invention is additionally excellent in control effect on insect pests that have a stinger or venom and harm humans and animals, insect pests that mediate various pathogens or disease-causing microbes, or insect pests that cause discomfort to humans (toxic pests, hygienic pests, and obnoxious pests, etc.).

Specific examples thereof will be shown below.

(1) Insect pests of the order Hymenoptera bees of the family Argidae, bees of the family Cynipidae, bees of the family Diprionidae, ants of the family Formicidae, bees of the family Mutillidae, and bees of the family Vespidae.

(2) Other insect pests

Blattodea, termites, Araneae, centipedes, millipedes, crustacea, and *Cimex lectularius*.

[Pharmaceutical Formulation]

Some pharmaceutical formulations of the pest control agent, the insecticide or acaricide, the ectoparasite control agent or the endoparasite control agent or expellant of the present invention will be shown. However, additives and addition ratios should not be limited by these examples and may be changed in wide ranges. The term "part" in the pharmaceutical formulations represents part by weight.

Hereinafter, the pharmaceutical formulations for agriculture or horticulture and for paddy rice will be shown.

(Preparation 1: Wettable Powder)

40 parts of the heteroaryl azole compound of the present invention, 53 parts of diatomaceous earth, 4 parts of higher alcohol sulfuric acid ester, and 3 parts of alkyl naphthalenesulfonate are uniformly mixed and finely milled to obtain a wettable powder containing 40% of the active ingredient.

(Preparation 2: Emulsion)

30 parts of the heteroaryl azole compound of the present invention, 33 parts of xylene, 30 parts of dimethylformamide, and 7 parts of polyoxyethylene alkyl allyl ether are mixed and dissolved to obtain an emulsion containing 30% of the active ingredient.

(Preparation 3: Granular Formulation)

5 parts of the heteroaryl azole compound of the present invention, 40 parts of talc, 38 parts of clay, 10 parts of bentonite, and 7 parts of sodium alkyl sulfate are uniformly mixed, finely milled, and then granulated into a granular shape of 0.5 to 1.0 mm in diameter to obtain a granular formulation containing 5% of the active ingredient.

(Preparation 4: Granular Formulation)

5 parts of the heteroaryl azole compound of the present invention, 73 parts of clay, 20 parts of bentonite, 1 part of dioctyl sulfosuccinate sodium salt, and 1 part of potassium phosphate are well milled and mixed, and after addition of water, the mixture is well kneaded, then granulated, and dried to obtain a granular formulation containing 5% of the active ingredient.

(Preparation 5: Suspension)

10 parts of the heteroaryl azole compound of the present invention, 4 parts of polyoxyethylene alkyl allyl ether, 2 parts of polycarboxylic acid sodium salt, 10 parts of glycerin, 0.2 parts of xanthan gum, and 73.8 parts of water are mixed and wet-milled until the particle size becomes 3 microns or smaller to obtain a suspension containing 10% of the active ingredient.

Hereinafter, the pharmaceutical formulations of the ectoparasite control agent or the endoparasite control agent or expellant will be shown.

(Preparation 6: Granules)

5 parts of the heteroaryl azole compound of the present invention are dissolved in an organic solvent to obtain a solution. The solution is sprayed onto 94 parts of kaolin and 1 part of white carbon. Then, the solvent is evaporated under reduced pressure. This type of granules may be mixed with animal feed.

(Preparation 7: Injectable Filler)

0.1 to 1 part of the heteroaryl azole compound of the present invention and 99 to 99.9 parts of peanut oil are uniformly mixed and then sterilized by filtration through a sterilizing filter.

(Preparation 8: Pore-On Formulation)

5 parts of the heteroaryl azole compound of the present invention, 10 parts of myristic acid ester, and 85 parts of isopropanol are uniformly mixed to obtain a pore-on formulation.

(Preparation 9: Spot-On Formulation)

10 to 15 parts of the heteroaryl azole compound of the present invention, 10 parts of palmitic acid ester, and 75 to 80 parts of isopropanol are uniformly mixed to obtain a spot-on formulation.

(Preparation 10: Spray Formulation)

1 part of the heteroaryl azole compound of the present invention, 10 parts of propylene glycol, and 89 parts of isopropanol are uniformly mixed to obtain a spray formulation.

Next, the present invention will be more specifically described with reference to Examples of compounds. However, the present invention is not limited by the following Examples of compounds by any means.

Example 1

Synthesis of 5'-(ethylsulfonyl)-6'-(5-methyl-1-(2,2,3,3,3-pentafluoropropyl)-1H-imidazol-4-yl)-2,3'-bipyridine (Compound No. c-1)

(Step 1) Synthesis of 1-(5-bromo-3-(ethylthio)pyridin-2-yl)propan-1-one

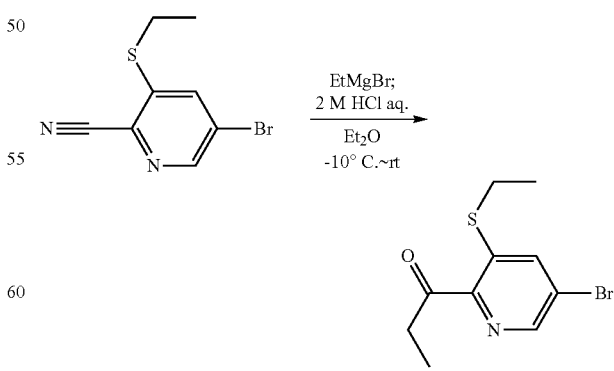

5-Bromo-3-(ethylthio)picolinonitrile (1.0 g) was dissolved in diethyl ether (8.2 ml), the reaction system was purged with nitrogen, followed by cooling to −10° C. Ethylmagnesium bromide (1.0 M, tetrahydrofuran solution, 4.9 ml) was added dropwise thereto, and the mixture was stirred at −10° C. for 30 minutes, then heated to room temperature, and stirred at room temperature for 1 hour. 2 M Hydrochloric acid (10 ml) was added thereto, and the mixture was stirred at room temperature for 15 minutes. The obtained solution was adjusted to a pH of 8 with an aqueous solution of 2 M sodium hydroxide, followed by extraction with ethyl acetate. The obtained organic layer was washed with saturated saline, dried over anhydrous magnesium sulfate, and filtered. The filtrate was concentrated under reduced pressure to obtain 1.2 g of the title compound (yield: quant.).

$^1$H-NMR of the obtained title compound will be shown below. $^1$H-NMR (400 MHz, CDCl$_3$): δ 8.38 (d, 1H), 7.75 (d, 1H), 3.15 (q, 2H), 2.88 (q, 2H), 1.38 (t, 3H), 1.18 (t, 3H).

(Step 2) Synthesis of 1-(5-bromo-3-(ethylthio)pyridin-2-yl)propan-1-one Oxime

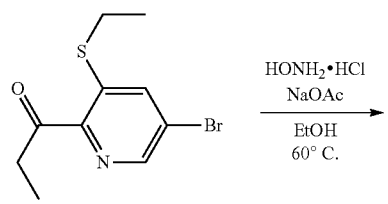

1-(5-Bromo-3-(ethylthio)pyridin-2-yl)propan-1-one (0.50 g) was dissolved in ethanol (9.1 ml), and the solution was stirred at room temperature. Hydroxylamine hydrochloride (0.15 g) and sodium acetate (0.22 g) were added thereto, and the mixture was stirred at 60° C. for 7 hours. The obtained solution was poured to water, followed by extraction with chloroform. The obtained organic layer was dried over anhydrous magnesium sulfate, and filtered. The filtrate was concentrated under reduced pressure, and the obtained residue (0.53 g) was used for the next step without being purified.

(Step 3) Synthesis of 1-(5-bromo-3-(ethylthio)pyridin-2-yl)propan-1-one O-tosyl Oxime

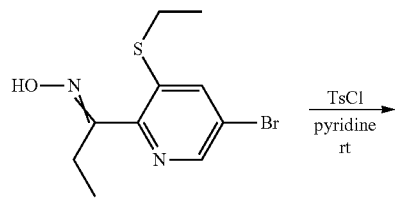

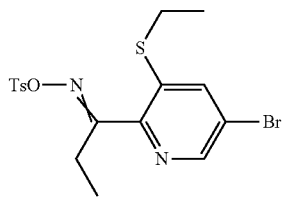

The concentrate (containing 1-(5-bromo-3-(ethylthio)pyridin-2-yl)propan-1-one oxime) obtained from step 2 was dissolved in pyridine (5.5 ml), and the solution was stirred at room temperature. Paratoluenesulfonyl (0.52 g) was added thereto, and the mixture was stirred at room temperature for 18 hours. The obtained solution was concentrated under reduced pressure, and the obtained concentrate was purified by silica gel column chromatography to obtain 0.27 g of the title compound (yield: 34%, two steps).

$^1$H-NMR of the obtained title compound will be shown below. $^1$H-NMR (400 MHz, CDCl$_3$): δ 8.42 (d, 1H), 7.82 (d, 2H), 7.77 (d, 1H), 7.31 (d, 2H), 2.92 (q, 2H), 2.59 (q, 2H), 2.44 (s, 3H), 1.29 (t, 3H), 1.07 (t, 3H).

(Step 4) Synthesis of 2-amino-1-(5-bromo-3-(ethylthio)pyridin-2-yl)propan-1-one

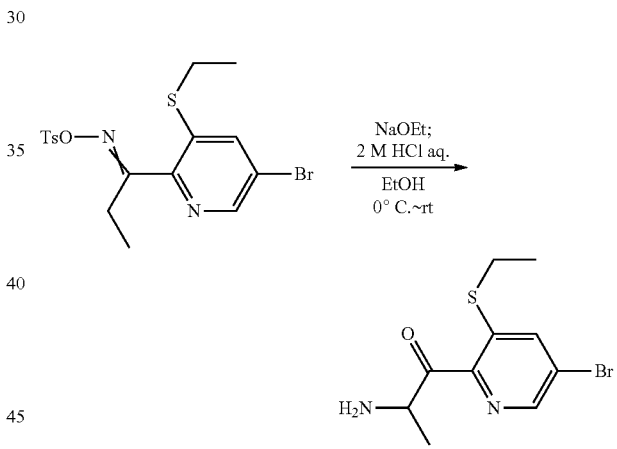

Sodium ethoxide (20%, ethanol solution, 0.084 g) was dissolved in ethanol (1.1 ml), and the solution was stirred at 0° C. An ethanol solution (1.2 ml) of 1-(5-bromo-3-(ethylthio)pyridin-2-yl)propan-1-one O-tosyl oxime (0.10 g) was added dropwise thereto, and the mixture was stirred at room temperature for 3 hours. The obtained solution was filtered with celite. 2 M Hydrochloric acid (2.0 ml) was added to the obtained filtrate, and the mixture was stirred at room temperature for 30 minutes. The obtained solution was poured to water, followed by extraction with 1 M hydrochloric acid and water. The obtained aqueous layer was concentrated under reduced pressure to obtain 0.060 g of the title compound (yield: 92%).

$^1$H-NMR of the obtained title compound will be shown below. $^1$H-NMR (400 MHz, DMSO-d$_6$): δ 8.60 (d, 1H), 8.13 (d, 1H), 5.06 (m, 1H), 3.04 (q, 2H), 1.39 (d, 3H), 1.24 (t, 3H).

(Step 5) Synthesis of 4-(5-bromo-3-(ethylthio)pyridin-2-yl)-5-methyl-1,3-dihydro-2H-imidazole-2-thione

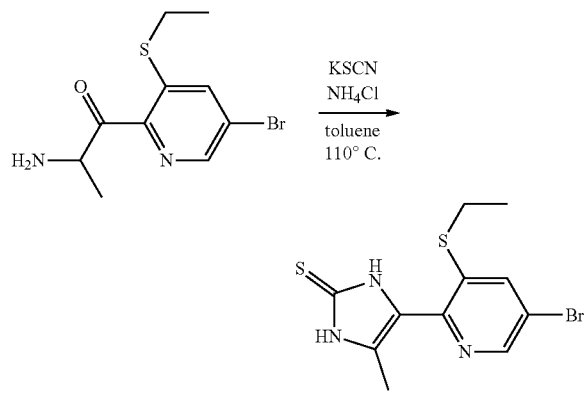

2-Amino-1-(5-bromo-3-(ethylthio)pyridin-2-yl)propan-1-one (0.10 g) was dissolved in toluene (3.5 ml), and the solution was stirred at room temperature. Potassium thiocyanate (0.17 g) and ammonium chloride (0.092 g) were added thereto, and the mixture was stirred at 110° C. for 4 hours. The solution was cooled to room temperature, the obtained solution was then poured to water, and the precipitated solid was filtered. The obtained solid was dried under reduced pressure to obtain 0.057 g of the title compound (yield: 50%).

$^1$H-NMR of the obtained title compound will be shown below. $^1$H-NMR (400 MHz, DMSO-$d_6$): δ 12.08 (brs, 1H), 11.99 (brs, 1H), 8.46 (d, 1H), 7.97 (d, 1H), 3.00 (q, 2H), 1.90 (s, 3H), 1.17 (t, 3H).

(Step 6) Synthesis of 5-bromo-3-(ethylthio)-2-(5-methyl-1H-imidazol-4-yl)pyridine

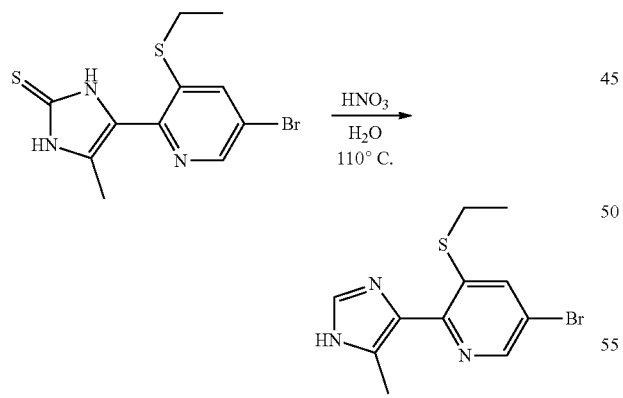

4-(5-Bromo-3-(ethylthio)pyridin-2-yl)-5-methyl-1,3-dihydro-2H-imidazole-2-thione (0.050 g) was suspended in water (1.4 ml), followed by stirring at room temperature. Nitric acid (0.15 ml) was added thereto, and the mixture was stirred at 110° C. for 1.5 hours. The solution was allowed to cool to room temperature, and the obtained solution was then poured to a 30% aqueous sodium hydroxide solution, followed by extraction with chloroform. The obtained organic layer was dried over anhydrous magnesium sulfate, and filtered. The obtained solution was concentrated under reduced pressure, and the obtained concentrate was purified by silica gel column chromatography to obtain 0.030 g of the title compound (yield: 66%).

$^1$H-NMR of the obtained title compound will be shown below. $^1$H-NMR (400 MHz, DMSO-$d_6$): δ 12.43 (brs, 1H), 8.70 (d, 1H), 8.26 (d, 1H), 7.69 (s, 1H), 3.29 (q, 2H), 2.52 (s, 3H), 1.08 (t, 3H).

(Step 7) Synthesis of 5-bromo-3-(ethylsulfonyl)-2-(5-methyl-1H-imidazol-4-yl)pyridine

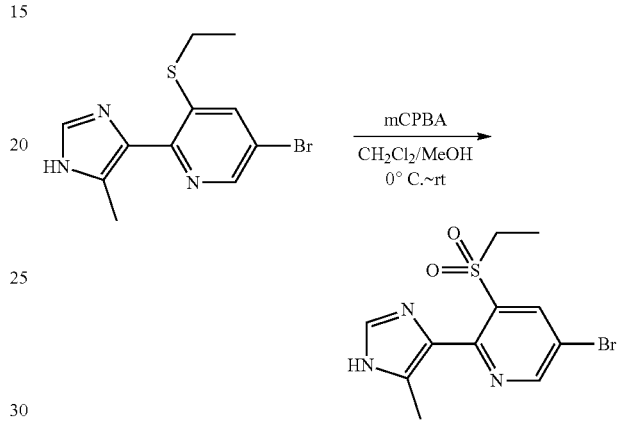

5-Bromo-3-(ethylthio)-2-(5-methyl-1H-imidazol-4-yl)pyridine (0.10 g) was dissolved in a mixed solvent of dichloromethane (6.7 ml) and methanol (0.34 ml), and the solution was stirred at 0° C. m-Chloroperbenzoic acid (70%, 0.18 g) was added thereto, and the mixture was stirred at room temperature for 2 hours. The obtained solution was poured to a mixed solution of a saturated aqueous solution of sodium bicarbonate and a saturated aqueous solution of sodium thiosulfate, followed by extraction with chloroform. The obtained organic layer was dried over anhydrous magnesium sulfate, and filtered. The obtained solution was concentrated under reduced pressure to obtain 0.11 g of the title compound (yield: 99%).

$^1$H-NMR of the obtained title compound will be shown below. $^1$H-NMR (400 MHz, DMSO-$d_6$): δ 12.28 (brs, 1H), 8.93 (d, 1H), 8.38 (d, 1H), 7.62 (s, 1H), 4.15 (q, 2H), 2.32 (s, 3H), 1.17 (t, 3H).

(Step 8) Synthesis of 5-bromo-3-(ethylsulfonyl)-2-(5-methyl-1-(2,2,3,3,3-pentafluoropropyl)-1H-imidazol-4-yl)pyridine

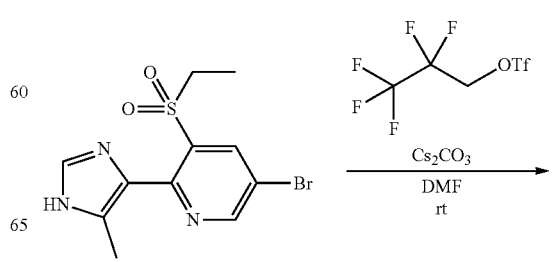

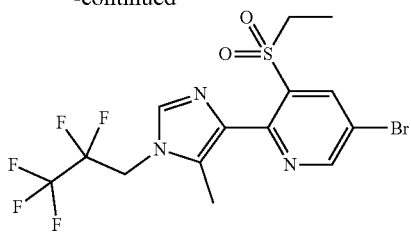

5-Bromo-3-(ethylsulfonyl)-2-(5-methyl-1H-imidazol-4-yl)pyridine (1.0 g) was dissolved in N,N-dimethylformamide (30 ml), and the solution was stirred at 0° C. 2,2,3,3,3-Pentafluoropropyl trifluoromethanesulfonate (1.3 g) and cesium carbonate (1.5 g) were added thereto, and the mixture was stirred at room temperature for 18 hours. The obtained solution was poured to a saturated aqueous solution of ammonium chloride, followed by extraction with ethyl acetate. The obtained organic layer was washed with saturated saline, dried over anhydrous magnesium sulfate, and filtered. The obtained solution was concentrated under reduced pressure, and the obtained concentrate was purified by silica gel column chromatography to obtain 1.1 g of the title compound (yield: 81%).

$^1$H-NMR of the obtained title compound will be shown below. $^1$H-NMR (400 MHz, CDCl$_3$): δ 8.85 (d, 1H), 8.57 (d, 1H), 7.54 (s, 1H), 4.48 (t, 2H), 3.95 (q, 2H), 2.37 (s, 3H), 1.33 (t, 3H).

(Step 9) Synthesis of 5'-(ethylsulfonyl)-6'-(5-methyl-1-(2,2,3,3,3-pentafluoropropyl)-1H-imidazol-4-yl)-2,3'-bipyridine

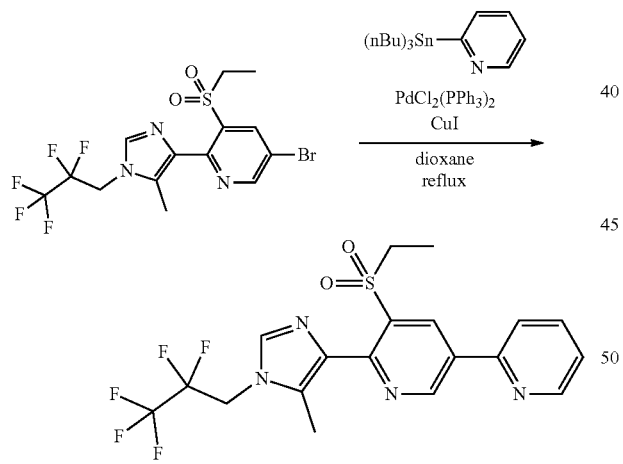

5-Bromo-3-(ethylsulfonyl)-2-(5-methyl-1-(2,2,3,3,3-pentafluoropropyl)-1H-imidazol-4-yl)pyridine (0.20 g) was dissolved in dioxane (4.3 ml), the reaction system was purged with nitrogen, followed by stirring at room temperature. Tributyl(2-pyridyl)tin (0.22 g), bis(triphenylphosphine)palladium (II) dichloride (0.030 g) and copper iodide (I) (0.016 g) were added thereto, and the mixture was stirred for 18 hours under heating to reflux. The obtained solution was poured to a saturated aqueous solution of potassium fluoride, and the mixture was filtered with celite. The obtained solution was extracted with ethyl acetate. The obtained organic layer was washed with saturated saline, dried over anhydrous magnesium sulfate, and filtered. The obtained solution was concentrated under reduced pressure, and the obtained concentrate was purified by silica gel column chromatography to obtain 0.16 g of the title compound (yield: 78%).

$^1$H-NMR of the obtained title compound will be shown below. $^1$H-NMR (400 MHz, CDCl$_3$): δ 9.47 (d, 1H), 9.01 (d, 1H), 8.77-8.75 (m, 1H), 7.85-7.84 (m, 2H), 7.57 (s, 1H), 7.36-7.32 (m, 1H), 4.50 (t, 2H), 3.96 (q, 2H), 2.41 (s, 3H), 1.35 (t, 3H).

Example 2

Synthesis of (Z)-5-cyclopropyl-3-(ethylsulfonyl)-2-(1-(2,3,3,4,4,5,5,5-octafluoropent-1-en-1-yl)-1H-1,2,4-triazol-3-yl)pyridine (Compound No. b-1)

(Step 1) Synthesis of 5-bromo-3-(ethylthio)picolinonitrile

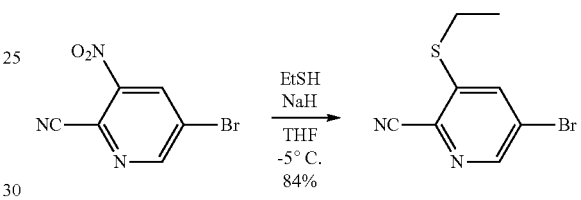

5-Bromo-3-nitropicolinonitrile (1 g) was dissolved in tetrahydrofuran (22 ml), the reaction vessel was purged with nitrogen, followed by cooling to −5° C. and stirring. Ca. 60% sodium hydride (0.2 g) was added thereto, the mixture was stirred for 5 minutes, ethylmercaptan (0.27 g) was then added dropwise, and the mixture was stirred at −5° C. for 30 minutes. The obtained solution was poured to water, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 0.90 g of the title compound (yield: 84%).

$^1$H-NMR of the obtained title compound will be shown below.
$^1$H-NMR (CDCl$_3$) δ: 8.50 (1H, d), 7.83 (1H, d), 3.07 (2H, q), 1.41 (3H, t).

(Step 2) Synthesis of 5-bromo-3-(ethylsulfonyl)picolinonitrile

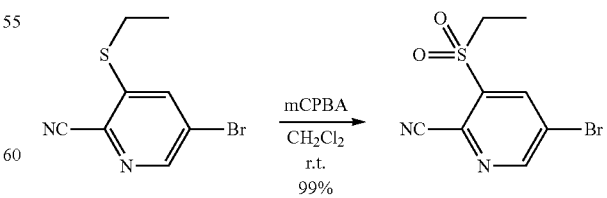

5-Bromo-3-(ethylthio)picolinonitrile (149 g) was dissolved in dichloromethane (1800 ml), and the solution was cooled to 0° C. and stirred. 70% m-chloroperbenzoic acid (333 g) was added thereto, and the mixture was stirred overnight at room temperature. The obtained solution was poured to a mixed solution of a saturated aqueous solution of sodium bicarbonate and a saturated aqueous solution of sodium thiosulfate, followed by extraction with dichloromethane. The obtained organic layer was washed with saturated saline, dried over anhydrous magnesium sulfate, and filtered. The filtrate was concentrated under reduced pressure, and the obtained residue was purified by silica gel column chromatography to obtain 167 g of the title compound (yield: 99%).

$^1$H-NMR of the obtained title compound will be shown below.

$^1$H-NMR (CDCl$_3$) δ: 9.26 (1H, d), 8.72 (1H, d), 3.60 (2H, q), 1.23 (3H, t).

(Step 3) Synthesis of 5-cyclopropyl-3-(ethylsulfonyl)picolinonitrile

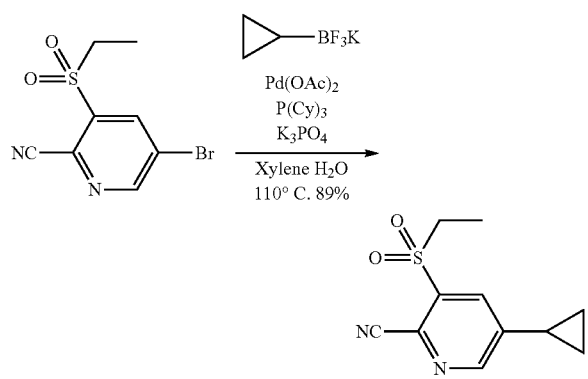

5-Bromo-3-(ethylthio)picolinonitrile (1.0 g) was dissolved in xylene (16 ml), the reaction vessel was purged with argon, and the solution was then stirred at room temperature. Potassium cyclopropyl trifluoroborate (1.3 g), palladium acetate (II) (0.16 g), a solution of 20% tricyclohexylphosphine in toluene (2.0 g), tripotassium phosphate (4.1 g), and water (2 ml) were added thereto, and the mixture was stirred overnight at 110° C. The obtained solution was poured to water, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 0.75 g of the title compound (yield: 89%).

$^1$H-NMR of the obtained title compound will be shown below.

$^1$H-NMR (CDCl$_3$) δ: 8.68 (1H, d), 7.94 (1H, d), 3.45 (2H, q), 2.10-2.03 (1H, m), 1.37 (3H, t), 1.35-1.30 (2H, m), 0.98-0.94 (2H, m).

(Step 4) Synthesis of 5-cyclopropyl-3-(ethylsulfonyl)picolinamide

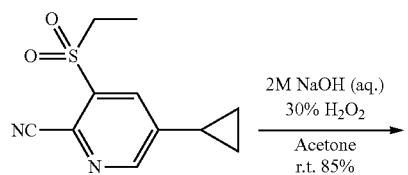

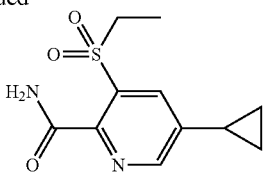

5-Cyclopropyl-3-(ethylsulfonyl)picolinonitrile (0.75 g) was dissolved in acetone (45 ml), and the solution was cooled to 0° C. An aqueous solution of 2 M sodium hydroxide (6.5 ml) and 30% hydrogen peroxide water (5 ml) were added dropwise thereto, and the mixture was stirred overnight at room temperature. The obtained solution was poured to a mixed solution of a saturated aqueous solution of sodium bicarbonate and a saturated aqueous solution of sodium thiosulfate, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 0.69 g of the title compound (yield: 85%).

$^1$H-NMR of the obtained title compound will be shown below.

$^1$H-NMR (CDCl$_3$) δ: 8.51 (1H, d), 8.09 (1H, d), 5.73 (2H, br s), 3.88 (2H, q), 2.09-2.02 (1H, m), 1.33 (3H, t), 1.24-1.19 (2H, m), 0.92-0.88 (2H, m).

(Step 5) Synthesis of 5-cyclopropyl-3-(ethylsulfonyl)-2-(1H-1,2,4-triazol-3-yl)pyridine

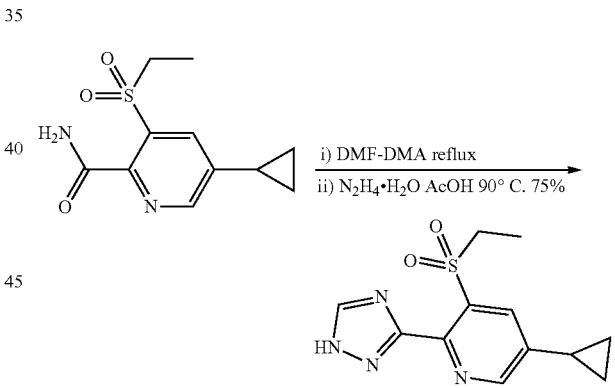

N,N-Dimethylformamide dimethyl acetal (11 ml) was added to 5-cyclopropyl-3-(ethylsulfonyl)picolinamide (0.69 g), and the mixture was stirred for 1 hour under heating to reflux. The obtained solution was concentrated under reduced pressure, acetic acid (14 ml) and hydrazine monohydrate (0.16 g) were added to the obtained residue, and the mixture was stirred at 90° C. for 1 hour. The obtained solution was concentrated under reduced pressure, and neutralized with a saturated aqueous solution of sodium bicarbonate, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 0.69 g of the title compound (yield: 85%).

$^1$H-NMR of the obtained title compound will be shown below.

$^1$H-NMR (CDCl$_3$) δ: 12.21 (1H, br s), 8.65 (1H, d), 8.19 (1H, s), 8.12 (1H, d), 3.96 (2H, q), 2.11-2.03 (1H, m), 1.33 (3H, t), 1.25-1.20 (2H, m), 0.94-0.90 (2H, m).

(Step 6) Synthesis of 5-cyclopropyl-3-(ethylsulfonyl)-2-(1-(2,2,3,3,4,4,5,5,5-nonafluoropentyl)-1H-1,2,4-triazol-3-yl)pyridine (Compound No. b-2)

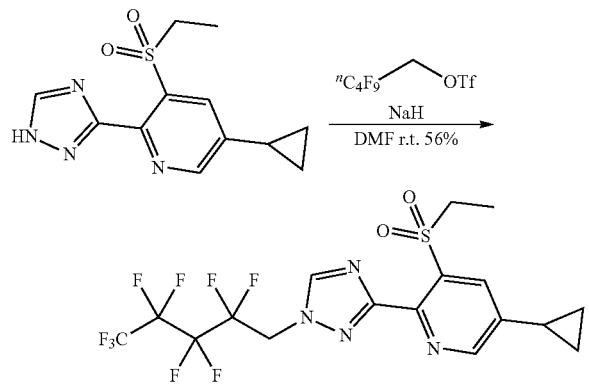

Ca. 55% sodium hydride (0.05 g) was suspended in N,N-dimethylformamide (10 ml), followed by stirring at 0° C. 5-Cyclopropyl-3-(ethylsulfonyl)-2-(1H-1,2,4-triazol-3-yl)pyridine (0.27 g) was added thereto, and the mixture was stirred at 0° C. for 30 minutes. 2,2,3,3,4,4,5,5,5-nonafluoropentyl trifluoromethanesulfonate (0.44 g) prepared by the method described in WO2005/063694 was added dropwise thereto, and the mixture was stirred overnight at room temperature. The obtained solution was poured to water, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 0.27 g of the title compound (yield: 56%)

$^1$H-NMR and $^{19}$F-NMR of the obtained title compound will be shown below.

$^1$H-NMR (CDCl$_3$) δ: 8.72 (1H, d), 8.31 (1H, s), 8.05 (1H, d), 4.95 (2H, t), 3.83 (2H, q), 2.10-2.04 (1H, m), 1.35 (3H, t), 1.23-1.18 (2H, m), 0.92-0.88 (2H, m); $^{19}$F-NMR (376 MHz, CDCl$_3$—C$_6$F$_6$): δ −81.30 (3F, tt), −117.42--117.60 (2F, m), −124.24--124.40 (2F, m), −126.34--136.49 (2F, m).

(Step 7) Synthesis of (Z)-5-cyclopropyl-3-(ethylsulfonyl)-2-(1-(2,3,3,4,4,5,5,5-octafluoropent-1-en-1-yl)-1H-1,2,4-triazol-3-yl)pyridine

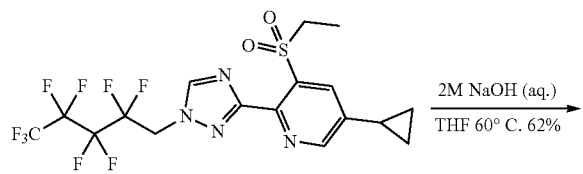

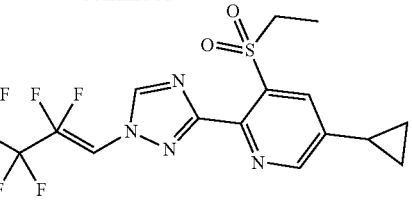

5-Cyclopropyl-3-(ethylsulfonyl)-2-(1-(2,2,3,3,4,4,5,5,5-nonafluoropentyl)-1H-1,2,4-triazol-3-yl)pyridine (0.24 g) was dissolved in tetrahydrofuran (9 ml), and the solution was stirred at room temperature. An aqueous solution of 2 M sodium hydroxide (1.2 ml) was added dropwise thereto, and the mixture was stirred overnight at 60° C. The obtained solution was poured a saturated aqueous solution of ammonium chloride, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 0.14 g of the title compound (yield: 62%).

$^1$H-NMR and $^{19}$F-NMR of the obtained title compound will be shown below.

$^1$H-NMR (CDCl$_3$) δ: 8.73 (1H, d), 8.72 (1H, d), 8.05 (1H, d), 7.41 (1H, d), 3.87 (2H, q), 2.12-2.05 (1H, m), 1.37 (3H, t), 1.25-1.20 (2H, m), 0.94-0.90 (2H, m); $^{19}$F-NMR (376 MHz, CDCl$_3$—C$_6$F$_6$): δ −81.01 (3F, t), −119.28--119.39 (2F, m), −127.35--127.40 (2F, m), −133.46--133.70 (1F, m).

Example 3

Synthesis of 5-cyclopropyl-3-(ethylsulfonyl)-2-(1-(5-(trifluoromethyl)pyridin-2-yl)-1H-1,2,4-triazol-3-yl)pyridine (Compound No. d-4)

(Step 1) Synthesis of 5-bromo-3-(ethylsulfonyl)picolinamide

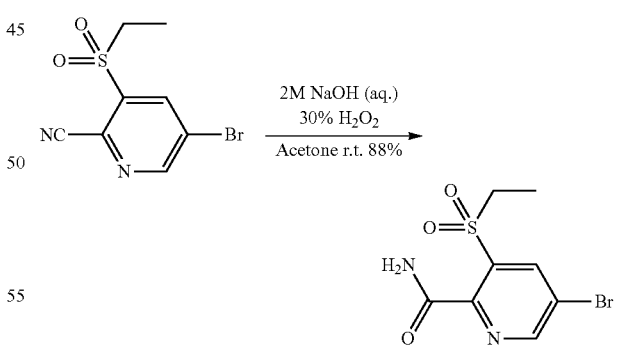

5-Bromo-3-(ethylsulfonyl)picolinonitrile (1.0 g) was dissolved in acetone (50 ml), and the solution was cooled to 0° C. An aqueous solution of 2 M sodium hydroxide (8.0 ml) and 30% hydrogen peroxide water (6.0 ml) were added dropwise thereto, and the mixture was stirred overnight at room temperature. The obtained solution was poured to a mixed solution of a saturated aqueous solution of sodium bicarbonate and a saturated aqueous solution of sodium thiosulfate, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 0.93 g of the title compound (yield: 88%).

¹H-NMR of the obtained title compound will be shown below.

¹H-NMR (CDCl₃) δ: 8.82 (1H, d), 8.68 (1H, d), 7.16 (1H, br s), 5.78 (1H, br s), 3.90 (2H, q), 1.36 (3H, t).

(Step 2) Synthesis of 5-bromo-3-(ethylsulfonyl)-2-(1H-1,2,4-triazol-3-yl)pyridine

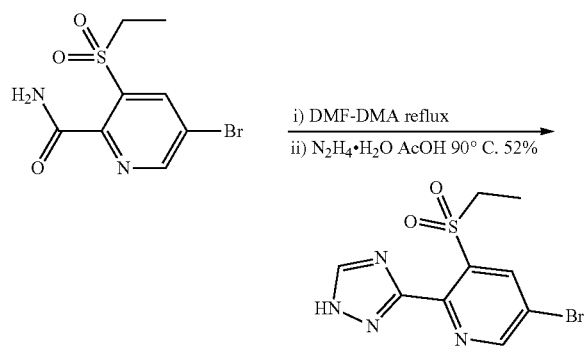

N,N-Dimethylformamide dimethyl acetal (13 ml) was added to 5-bromo-3-(ethylsulfonyl)picolinamide (0.93 g), and the mixture was stirred for 1 hour under heating to reflux. The obtained solution was concentrated under reduced pressure, and acetic acid (16 ml) and hydrazine monohydrate (0.19 g) were added to the obtained residue, and the mixture was stirred at 90° C. for 1 hour. The obtained solution was concentrated under reduced pressure, and neutralized with a saturated aqueous solution of sodium bicarbonate, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 0.53 g of the title compound (yield: 52%).

¹H-NMR of the obtained title compound will be shown below.

¹H-NMR (CDCl₃) δ: 11.72 (1H, br s), 8.95 (1H, d), 8.72 (1H, d), 8.24 (1H, s), 4.03 (2H, q), 1.37 (3H, t).

(Step 3) Synthesis of 5-bromo-3-(ethylsulfonyl)-2-(1-(5-(trifluoromethyl)pyridin-2-yl)-1H-1,2,4-triazol-3-yl)pyridine

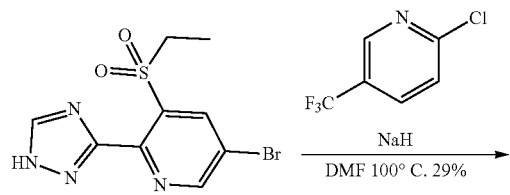

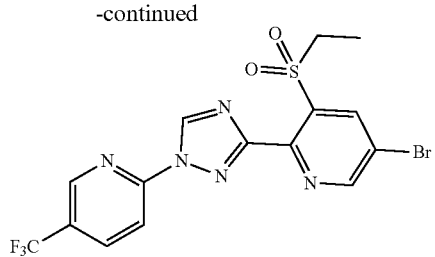

Ca. 55% sodium hydride (0.084 g) was suspended in N,N-dimethylformamide (16 ml), followed by stirring at 0° C. 5-Bromo-3-(ethylsulfonyl)-2-(1H-1,2,4-triazol-3-yl)pyridine (0.50 g) was added thereto, and the mixture was stirred at 0° C. for 30 minutes. 2-Chloro-5-(trifluoromethyl)pyridine (0.34 g) was added thereto, and the mixture was stirred at 100° C. for 4 hours. The obtained solution was poured to water, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 0.22 g of the title compound (yield: 29%).

¹H-NMR of the obtained title compound will be shown below.

¹H-NMR (CDCl₃) δ: 9.32 (1H, s), 9.05 (1H, d), 8.78 (1H, s), 8.67 (1H, d), 8.18-8.10 (2H, m), 3.98 (2H, q), 1.43 (3H, t).

(Step 4) Synthesis of 5-cyclopropyl-3-(ethylsulfonyl)-2-(1-(5-(trifluoromethyl)pyridin-2-yl)-1H-1,2,4-triazol-3-yl)pyridine

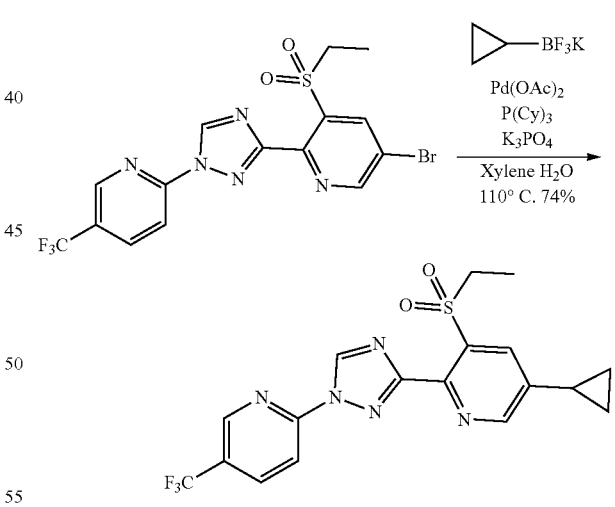

5-Bromo-3-(ethylsulfonyl)-2-(1-(5-(trifluoromethyl)pyridin-2-yl)-1H-1,2,4-triazol-3-yl)pyridine (0.11 g) was dissolved in xylene (2.2 ml), and the reaction vessel was purged with argon, followed by stirring at room temperature. Potassium cyclopropyl trifluoroborate (0.089 g), palladium acetate (II) (0.011 g), a solution of 20% tricyclohexylphosphine in toluene (0.13 g), tripotassium phosphate (0.27 g) and water (0.22 ml) were added thereto, and the mixture was stirred overnight at 110° C. The obtained solution was poured to water, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 0.075 g of the title compound (yield: 74%).

¹H-NMR of the obtained title compound will be shown below.

¹H-NMR (CDCl₃) δ: 9.30 (1H, s), 8.76 (1H, s), 8.75 (1H, d), 8.16-8.11 (2H, m), 8.08 (1H, d), 3.93 (2H, q), 2.13-2.06 (1H, m), 1.39 (3H, t), 1.28-1.20 (2H, m), 0.95-0.90 (2H, m).

Example 4

Synthesis of 5-cyclopropyl-3-(ethylsulfonyl)-2-(1-(4-(trifluoromethoxy)phenyl)-1H-imidazol-4-yl)pyridine (Compound No. d-19)

Step 1

Synthesis of 2-bromo-1-(5-bromo-3-(ethylthio)pyridin-2-yl)ethan-1-one

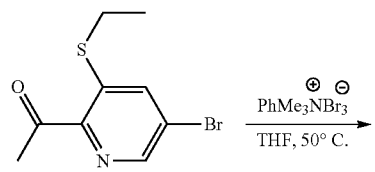

1-(5-Bromo-3-(ethylthio)pyridin-2-yl)ethan-1-one (1.95 g) was dissolved in tetrahydrofuran (40 ml), phenyltrimethylammonium tribromide was then added, and the mixture was stirred overnight at 50° C. The obtained solution was poured to a mixed solution of a saturated aqueous solution of sodium bicarbonate and a saturated aqueous solution of sodium thiosulfate, followed by extraction with ethyl acetate. The obtained organic layer was washed with saturated saline, dried over anhydrous magnesium sulfate, and filtered. The filtrate was concentrated under reduced pressure, and the obtained residue was purified by silica gel column chromatography to obtain 1.02 g of the title compound (yield: 40%).

¹H-NMR of the obtained title compound will be shown below.

¹H-NMR (CDCl₃) δ: 8.41 (1H, d), 7.80 (1H, d), 4.77 (2H, s), 2.93 (2H, q), 1.42 (3H, t).

Step 2

Synthesis of 1-(5-bromo-3-(ethylthio)pyridin-2-yl)-2-((4-(trifluoromethoxy)phenyl)amino)ethan-1-one 2-Bromo-1-(5-bromo-3-(ethylthio)pyridin-2-yl)ethan-1-one (1.36 g) was dissolved in N,N-dimethylformamide (20 ml), and the solution was cooled to 0° C. and stirred. 4-(Trifluoromethoxy)aniline (0.78 g) and potassium carbonate (0.66 g) were added thereto, and the mixture was stirred at room temperature for 3 hours. The obtained solution was poured to water, followed by extraction with ethyl acetate. The obtained organic layer was washed with saturated saline, dried over anhydrous magnesium sulfate, and filtered. The filtrate was concentrated under reduced pressure, and the obtained residue was washed with hexane to obtain 1.46 g of the title compound (yield: 83%).

¹H-NMR of the obtained title compound will be shown below.

¹H-NMR (CDCl₃) δ: 8.44 (1H, d), 7.82 (1H, d), 7.06 (2H, d), 6.67 (2H, d), 4.94-4.87 (1H, brs), 4.75 (2H, d), 2.95 (2H, q), 1.43 (3H, t).

Step 3

Synthesis of 4-(5-bromo-3-(ethylthio)pyridin-2-yl)-1-(4-(trifluoromethoxy)phenyl)-1,3-dihydro-2H-imidazole-2-thione 1-(5-Bromo-3-(ethylthio)pyridin-2-yl)-2-((4-(trifluoromethoxy)phenyl)amino)ethan-1-one (1.46 g) was dissolved in acetic acid (10 ml). Potassium thiocyanate (0.65 g) was added thereto, and the mixture was stirred at 100° C. for 30 minutes. The obtained solution was concentrated under reduced pressure, and neutralized with a saturated aqueous solution of sodium bicarbonate, followed by extraction with ethyl acetate. The obtained organic layer was washed with saturated saline, dried over anhydrous magnesium sulfate, and filtered. The filtrate was concentrated under reduced pressure, and the obtained residue was washed with diethyl ether to obtain 0.66 g of the title compound (yield: 41%).

$^1$H-NMR of the obtained title compound will be shown below.

$^1$H-NMR (CDCl$_3$) δ: 10.30-10.19 (1H, br), 8.45 (1H, d), 7.83 (1H, d), 7.79-7.74 (3H, m), 7.40-7.35 (2H, m), 3.07 (2H, q), 1.40 (3H, t).

Step 4

Synthesis of 5-bromo-3-(ethylsulfinyl)-2-(1-(4-(trifluoromethoxy)phenyl)-1H-imidazol-4-yl)pyridine

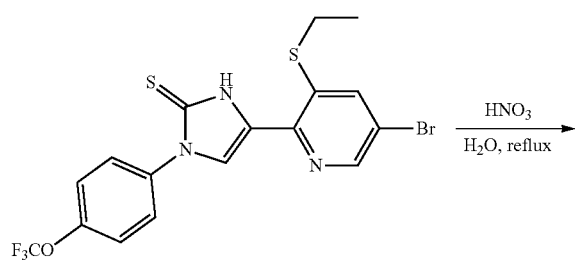

4-(5-Bromo-3-(ethylthio)pyridin-2-yl)-1-(4-(trifluoromethoxy)phenyl)-1,3-dihydro-2H-imidazole-2-thione (0.66 g) was suspended in water (9 ml). Fuming nitric acid (1 ml) was added thereto, and the mixture was stirred for 1 hour under heating to reflux. The obtained solution was neutralized with a 25% aqueous sodium hydroxide solution, followed by extraction with ethyl acetate. The obtained organic layer was washed with saturated saline, dried over anhydrous magnesium sulfate, and filtered. The filtrate was concentrated under reduced pressure, and the obtained residue was used for the next step without being purified.

Step 5

Synthesis of 5-bromo-3-(ethylsulfonyl)-2-(1-(4-(trifluoromethoxy)phenyl)-1H-imidazol-4-yl)pyridine

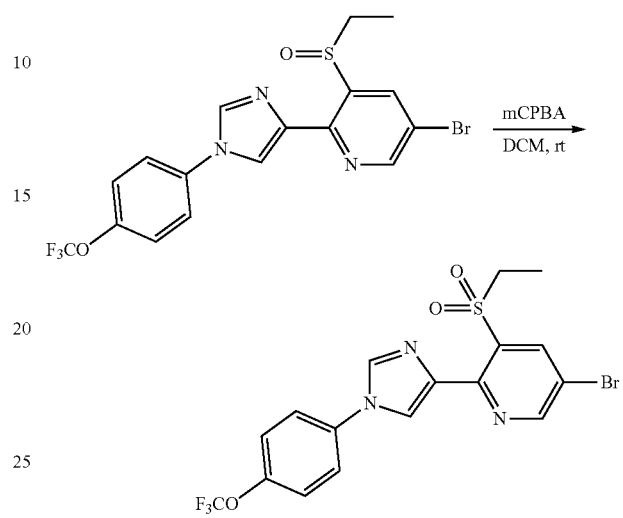

The 5-bromo-3-(ethylsulfinyl)-2-(1-(4-(trifluoromethoxy)phenyl)-1H-imidazol-4-yl)pyridine obtained from step 4 was dissolved in dichloromethane, and the solution was stirred at 0° C. m-Chloroperbenzoic acid (70%, 0.37 g) was added thereto, and the mixture was stirred at room temperature for 1 hour. The obtained solution was poured to a mixed solution of a saturated aqueous solution of sodium bicarbonate and a saturated aqueous solution of sodium thiosulfate, followed by extraction with dichloromethane. The obtained organic layer was washed with saturated saline, dried over anhydrous magnesium sulfate, and filtered. The filtrate was concentrated under reduced pressure, and the obtained residue was purified by silica gel column chromatography to obtain 0.56 g of the title compound (yield: 35%, two steps).

$^1$H-NMR of the obtained title compound will be shown below.

$^1$H-NMR (CDCl$_3$) δ: 8.85 (1H, d), 8.64 (1H, d), 8.00 (1H, d), 7.91 (1H, d), 7.54-7.48 (2H, m), 7.42-7.35 (2H, m), 4.00 (2H, q), 1.35 (3H, t).

Step 6

Synthesis of 5-cyclopropyl-3-(ethylsulfonyl)-2-(1-(4-(trifluoromethoxy)phenyl)-1H-imidazol-4-yl)pyridine

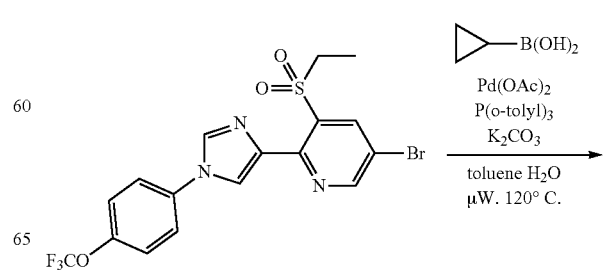

-continued

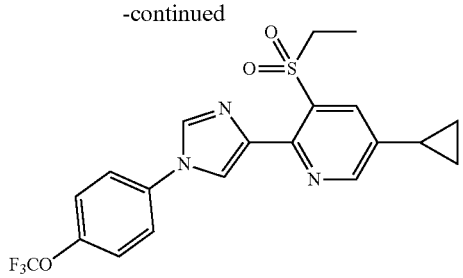

5-Bromo-3-(ethylsulfonyl)-2-(1-(4-(trifluoromethoxy)phenyl)-1H-imidazol-4-yl)pyridine (0.13 g) and toluene (4 ml) were added to a microwave synthesis reaction vessel. Cyclopropylboronic acid (0.070 g), palladium acetate (II) (0.0070 g), tri(o-tolyl)phosphine (0.018 g), potassium carbonate (0.11 g) and water (0.5 ml) were added thereto, and the mixture was reacted at 120° C. for 1 hour using a microwave synthesis apparatus. The obtained solution was poured to water, followed by extraction with ethyl acetate. The obtained organic layer was washed with saturated saline, dried over anhydrous magnesium sulfate, and filtered. The filtrate was concentrated under reduced pressure, and the obtained residue was purified by silica gel chromatography to obtain 0.080 g of the title compound (yield: 67%).

$^1$H-NMR of the obtained title compound will be shown below.

$^1$H-NMR (CDCl$_3$) δ: 8.62 (1H, d), 8.08 (1H, d), 7.93 (1H, d), 7.90 (1H, d), 7.54-7.48 (2H, m), 7.40-7.34 (2H, m), 3.84 (2H, q), 2.07-1.99 (1H, m), 1.30 (3H, t), 1.19-1.12 (2H, m), 0.90-0.83 (2H, m).

Examples of the heteroaryl azole compounds of the present invention produced in the same way as in Examples described above are shown in Tables 1 to 4. Table 1 shows the substituents of the compound of formula (I-1). Table 2 shows the substituents of the compound of formula (III-1). The physical property data of the compounds is described in the columns of "physical properties". Properties or melting points (m.p.) are described as physical property data. When R is a substituted or unsubstituted C1-6 alkenyl group, the configuration of the double bond of the C1-6 alkenyl group is described in the column of "conformation". "E" represents an E-configuration, "Z" represents a Z-configuration, and "E/Z" means that the compound is a mixture of compounds of E- and Z-configurations.

In the tables, Me represents a methyl group, Et represents an ethyl group, and $^c$Pr represents a cyclopropyl group.

TABLE 1

| Compound No. | R$^1$ | R$^2$ | R$^3$ | R | (X)$_n$ | Conformation | Physical properties. |
|---|---|---|---|---|---|---|---|
| a-1 | SO$_2$Et | Me | H | CH=C(F)CF$_2$CF$_2$CF$_3$ | 5-CF$_3$ | Z | m.p.: 147-149 (° C.) |
| a-2 | SO$_2$Et | Me | H | CH$_2$CF$_2$CF$_2$CF$_2$CF$_3$ | 5-CF$_3$ | — | m.p.: 111-113 (° C.) |
| a-3 | SO$_2$Et | Me | H | CH=C(F)CHFCF$_3$ | 5-$^c$Pr | Z | m.p.: 173-176 (° C.) |
| a-4 | SO$_2$Et | Me | H | CH=C(F)CF$_2$CF$_3$ | 5-CF$_3$ | Z | m.p.: 159-161 (° C.) |
| a-5 | SO$_2$Et | Me | H | CH$_2$CF$_2$CF$_2$CF$_3$ | 5-CF$_3$ | — | m.p.: 109-111 (° C.) |
| a-6 | SO$_2$Et | Me | H | CH=C(F)CF$_2$CF$_3$CF$_2$ | — | Z | m.p.: 179-181 (° C.) |
| a-7 | SO$_2$Et | Me | H | CH=C(F)CF$_2$CF$_3$ | — | Z | m.p.: 193-195 (° C.) |
| a-8 | SO$_2$Et | Me | H | CH$_2$CF$_2$CF$_2$CF$_2$CF$_3$ | — | — | m.p.: 64-66 (° C.) |
| a-9 | SO$_2$Et | Me | H | CH$_2$CF$_2$CF$_2$CF$_3$ | — | — | m.p.: 100-102 (° C.) |
| a-10 | SO$_2$Et | Me | H | CH$_2$CF$_2$CHFCF$_3$ | 5-$^c$Pr | — | m.p.: 116-118 (° C.) |
| a-11 | SO$_2$Et | Me | H | CH=C(F)CF$_3$ | — | Z | m.p.: 213-215 (° C.) |
| a-12 | SO$_2$Et | Me | H | CH$_2$CF$_3$CF$_3$ | — | — | m.p.: 96-98 (° C.) |
| a-13 | SO$_2$Et | Me | H | CH=O(F)CF$_2$CF$_2$ | 5-$^c$Pr | Z | m.p.: 155-157 (° C.) |
| a-14 | SO$_2$Et | Me | H | CH=C(F)CF$_3$ | 5-$^c$Pr | Z | m.p.: 163-165 (° C.) |
| a-15 | SO$_2$Et | Me | H | CH$_2$CF$_2$CF$_2$CF$_2$CHF$_2$ | 5-(pyrimidin-2-yl) | — | m.p.: 112-114 (° C.) |
| a-16 | SO$_2$Et | Me | H | CH$_2$CF$_2$CF$_3$CF$_2$ | 5-(pyridin-2-yl) | — | m.p.: 1183-185 (° C.) |
| a-17 | SO$_2$Et | Me | H | CH=C(F)CF$_2$CF$_3$ | 6-(1H-1,2,4-triazol-1-yl) | Z | m.p.: 162-184 (° C.) |
| a-18 | SO$_2$Et | Me | H | CF=CHFOCF$_2$CF$_2$CF$_3$ | 5-CF$_3$ | E/Z | amorphous |
| a-19 | SO$_2$Et | Me | H | CF$_2$CHFOCF$_2$CF$_2$CF$_3$ | 5-CF$_3$ | — | viscous oil |

TABLE 1

| Compound No. | R$^1$ | R$^2$ | R$^3$ | R | (X)$_n$ | Conformation | Physical properties. |
|---|---|---|---|---|---|---|---|
| a-1 | SO$_2$Et | Me | H | CH=C(F)CF$_2$CF$_2$CF$_3$ | 5-CF$_3$ | Z | m.p.: 147-149(° C.) |
| a-2 | SO$_2$Et | Me | H | CH$_2$CF$_2$CF$_2$CF$_2$CF$_3$ | 5-CF$_3$ | — | m.p.: 111-113(° C.) |
| a-3 | SO$_2$Et | Me | H | CH=C(F)CHFCF$_3$ | 5-$^c$Pr | Z | m.p.: 173-176(° C.) |
| a-4 | SO$_2$Et | Me | H | CH=C(F)CF$_2$CF$_3$ | 5-CF$_3$ | Z | m.p.: 159-161(° C.) |
| a-5 | SO$_2$Et | Me | H | CH$_2$CF$_2$CF$_2$CF$_2$ | 5-CF$_3$ | — | m.p.: 109-111(° C.) |
| a-6 | SO$_2$Et | Me | H | CH=C(F)CF$_2$CF$_3$CF$_2$ | — | Z | m.p.: 179-181(° C.) |
| a-7 | SO$_2$Et | Me | H | CH=C(F)CF$_2$CF$_2$ | — | Z | m.p.: 193-195(° C.) |
| a-8 | SO$_2$Et | Me | H | CH$_2$CF$_2$CF$_2$CF$_2$CF$_3$ | — | — | m.p.: 64-66(° C.) |
| a-9 | SO$_2$Et | Me | H | CH$_2$CF$_2$CF$_2$CF$_3$ | — | — | m.p.: 100-102(° C.) |
| a-10 | SO$_2$Et | Me | H | CH$_2$CF$_2$CHFCF$_3$ | 5-$^c$Pr | — | m.p.: 116-118(° C.) |
| a-11 | SO$_2$Et | Me | H | CH=C(F)CF$_3$ | — | Z | m.p.: 213-215(° C.) |
| a-12 | SO$_2$Et | Me | H | CH$_2$CF$_3$CF$_3$ | — | — | m.p.: 96-98(° C.) |
| a-13 | SO$_2$Et | Me | H | CH=C(F)CF$_2$CF$_3$ | 5-$^c$Pr | Z | m.p.: 155-157(° C.) |
| a-14 | SO$_2$Et | Me | H | CH=C(F)CF$_3$ | 5-$^c$Pr | Z | m.p.: 163-165(° C.) |
| a-15 | SO$_2$Et | Me | H | CH$_2$CF$_2$CF$_2$CF$_2$CHF$_2$ | 5-(pyrimidin-2-yl) | — | m.p.: 112-114(° C.) |
| a-16 | SO$_2$Et | Me | H | CH$_2$CF$_2$CF$_3$CF$_3$ | 5-(pyridin-2-yl) | — | m.p.: 183-185(° C.) |

TABLE 1-continued

| Compound No. | R¹ | R² | R³ | R | $(X)_n$ | Conformation | Physical properties. |
|---|---|---|---|---|---|---|---|
| a-17 | SO₂Et | Me | H | CH=C(F)CF₂CF₃ | 6-(1H-1,2,4-triazol-1-yl) | Z | m.p.: 182-184(° C.) |
| a-18 | SO₂Et | Me | H | CF=CHOCF₂CF₂CF₃ | 5-CF₃ | E/Z | amorphous |
| a-19 | SO₂Et | Me | H | CF₂CHFOCF₂CF₂CF₃ | 5-CF₃ | — | viscous oil |

TABLE 2

| Compound No. | R¹ | R² | R | $(X)_n$ | Conformation | Physical properties. |
|---|---|---|---|---|---|---|
| b-1 | SO₂Et | H | CH=C(F)CF₂CF₂CF₃ | 5-ⁿPr | Z | m.p.: 102-104 (° C.) |
| b-2 | SO₂Et | H | CH₂CF₂CF₂CF₂CF₃ | 5-ⁿPr | — | m.p.: 190-193 (° C.) |
| b-3 | SO₂Et | H | CH=C(F)CF₂CF₃ | 5-(3,5-F₂-phenyl) | Z | m.p.: 138-140 (° C.) |
| b-4 | SO₂Et | H | CH=C(F)CF₃ | — | Z | m.p.: 155-157 (° C.) |
| b-5 | SO₂Et | H | CH=C(F)CF₂CF₂CF₃ | — | Z | m.p.: 144-146 (° C.) |
| b-6 | SO₂Et | H | CH₂CF₂CF₃ | — | — | m.p.: 112-115 (° C.) |
| b-7 | SO₂Et | H | CH₂CF₂CF₂CF₂CF₃ | — | — | m.p.: 135-137 (° C.) |
| b-8 | SO₂Et | H | CH=C(F)CF₂CF₃ | — | Z | m.p.: 152-154 (° C.) |
| b-9 | SO₂Et | H | CH₂CF₂CF₂CF₃ | — | — | m.p.: 137-138 (° C.) |
| b-10 | SO₂Et | H | CH=C(F)CF₂CF₃ | 5-ⁿPr | Z | m.p.: 102-104 (° C.) |
| b-11 | SO₂Et | H | CH₂CF₂CF₂CF₃ | 5-ⁿPr | — | m.p.: 180-182 (° C.) |
| b-12 | SO₂Et | H | CH=C(F)CF₂CF₃ | 5-(pyrimidin-2-yl) | Z | m.p.: 255-260 (° C.) |
| b-13 | SO₂Et | H | CH₂CF₂CF₂CF₃ | 5-(pyrimidin-2-yl) | — | m.p.: 261-265 (° C.) |
| b-14 | SO₂Et | H | CH₂CF₂CF₂CF₃ | 5-Br | — | m.p.: 205-207 (° C.) |
| b-15 | SO₂Et | H | CH₂CF₂CF₂CF₃ | 6-(ethylsulfonyl) | — | m.p.: 211-213 (° C.) |
| b-16 | SO₂Et | H | CH₂CF₂CF₂CF₃ | 6-(1H-1,2,4-triazol-1-yl) | — | m.p.: 244-246 (° C.) |
| b-17 | SO₂Et | H | CH=C(F)CF₂CF₃ | 6-(1H-1,2,4-triazol-1-yl) | Z | m.p.: 202-204 (° C.) |
| b-18 | SO₂Et | H | CH₂CF₂CF₂CF₂CF₃ | 6-(1H-1,2,4-triazol-1-yl) | — | m.p.: 242-246 (° C.) |
| b-19 | SO₂Et | H | CH=C(F)CF₂CF₂CF₂ | 6-(1H-1,2,4-triazol-1-yl) | Z | m.p.: 200-202 (° C.) |
| b-20 | SO₂Et | H | CH=C(F)CF₂CF₂CHF₂ | 5-Br | Z | m.p.: 118-120 (° C.) |
| b-21 | SO₂Et | H | CH=C(F)CF₂CF₂CHF₂ | 5-ⁿPr | Z | viscous oil |
| b-22 | SO₂Et | H | CH=C(F)CF₂CF₂CF₂ | 5-(1-Me-ⁿPr) | Z | m.p.: 144-146 (° C.) |
| b-23 | SO₂Et | H | CF₂CHFOCF₂CF₂CF₃ | 5-ⁿPr | — | viscous oil |
| b-24 | SO₂Et | H | CF₂CHFOCF₃ | 5-(pyrimidin-2-yl) | — | m.p.: 110-114 (° C.) |
| b-25 | SO₂Et | H | CF₂CHFOCF₃ | 5-ⁿPr | — | $n_0$ (19.7° C.); 1.491 |

TABLE 2

| Compound No | R¹ | R² | R³ | $(X)_n$ | Conformation | Physical properties. |
|---|---|---|---|---|---|---|
| b-1 | SO₂Et | H | CH=C(F)CF₂CF₂CF₃ | 5-ⁿPr | Z | m.p.: 102-104(° C.) |
| b-2 | SO₂Et | H | CH₂CF₂CF₂CF₂CF₃ | 5-ⁿPr | — | m.p.: 190-193(° C.) |
| b-3 | SO₂Et | H | CH=C(F)CF₂CF₃ | 5-(3,5-F₂-phenyl) | Z | m.p.: 138-140(° C.) |
| b-4 | SO₂Et | H | CH=C(F)CF₃ | — | Z | m.p.: 155-157(° C.) |
| b-5 | SO₂Et | H | CH=C(F)CF₃CF₂CF₃ | — | Z | m.p.: 144-146(° C.) |
| b-6 | SO₂Et | H | CH₂CF₂CF₃ | — | — | m.p.: 112-115(° C.) |
| b-7 | SO₂Et | H | CH₃CF₂CF₂CF₂CF₃ | — | — | m.p.: 135-137(° C.) |
| b-8 | SO₂Et | H | CH=C(F)CF₂CF₃ | — | Z | m.p.: 152-154(° C.) |
| b-9 | SO₂Et | H | CH₂CF₂CF₂CF₃ | — | — | m.p.: 137-138(° C.) |
| b-10 | SO₂Et | H | CH=C(F)CF₂CF₃ | 5-ⁿPr | Z | m.p.: 102-104(° C.) |
| b-11 | SO₂Et | H | CH₃CF₂CF₂CF₃ | 5-ⁿPr | — | m.p.: 180-182(° C.) |
| b-12 | SO₂Et | H | CH=C(F)CF₂CF₃ | 5-(pyrimidin-2-yl) | Z | m.p.: 255-260(° C.) |
| b-13 | SO₂Et | H | CH₂CF₂CF₂CF₃ | 5-(pyrimidin-2-yl) | — | m.p.: 261-265(° C.) |
| b-14 | SO₂Et | H | CH₃CF₂CF₂CF₃ | 5-Br | — | m.p.: 205-207(° C.) |
| b-15 | SO₂Et | H | CH₂CF₂CF₂CF₃ | 6-(ethylsulfonyl)) | — | m.p.: 211-213(° C.) |
| b-16 | SO₂Et | H | CH₂CF₂CF₃CF₂ | 6-(1H-1,2,4-triazol-1-yl) | — | m.p.: 244-246(° C.) |
| b-17 | SO₂Et | H | CH=C(F)CF₂CF₃ | 6-(1H-1,2,4-triazol-1-yl) | Z | m.p.: 202-204(° C.) |
| b-18 | SO₂Et | H | CH₃CF₂CF₂CF₂CF₃ | 6-(1H-1,2,4-triazol-1-yl) | — | m.p.: 242-246(° C.) |
| b-19 | SO₂Et | H | CH=C(F)CF₃CF₂CF₂ | 6-(1H-1,2,4-triazol-1-yl) | Z | m.p.: 200-202(° C.) |
| b-20 | SO₂Et | H | CH=C(F)CF₂CF₂CHF₂ | 5-Br | Z | m.p.: 118-120(° C.) |
| b-21 | SO₂Et | H | CH=C(F)CF₂CF₂CHF₂ | 5-ⁿPr | Z | viscous oil |
| b-22 | SO₂Et | H | CH=C(F)CF₂CF2CF₂ | 5-(1-Me-ⁿPr) | Z | m.p.: 144-146(° C.) |
| b-23 | SO₂Et | H | CF₂CHFOCF₂CF₂CF₃ | 5-ⁿPr | — | viscous off |
| b-24 | SO₂Et | H | CF₂CHFOCF₃ | 5-(pyrimidin-2-yl) | — | m.p.: 110-114(° C.) |
| b-25 | SO₂Et | H | CF₂CHFOCF₃ | 5-ⁿPr | — | $n_0$ (19.7° C.); 1.491 |

TABLE 3

| Compound No. | Structure | Physical properties |
|---|---|---|
| c-1 | 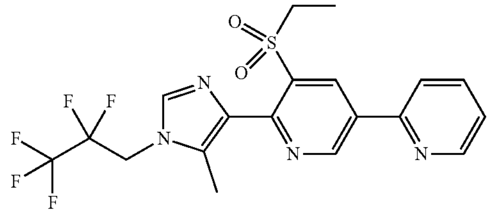 [SMILES: CCS(=O)(=O)c1cc(-c2ccccn2)cnc1-c1ncn(CC(F)(F)C(F)(F)F)c1C] | m.p.: 151-153 (° C.) |
| c-2 | 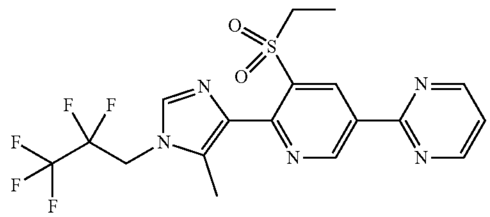 [SMILES: CCS(=O)(=O)c1cc(-c2ncccn2)cnc1-c1ncn(CC(F)(F)C(F)(F)F)c1C] | m.p.: 142-144 (° C.) |
| c-3 | 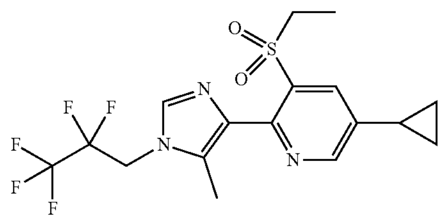 [SMILES: CCS(=O)(=O)c1cc(C2CC2)cnc1-c1ncn(CC(F)(F)C(F)(F)F)c1C] | m.p.: 120-122 (° C.) |
| c-4 | 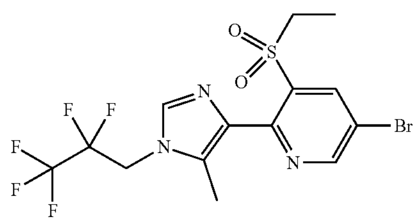 [SMILES: CCS(=O)(=O)c1cc(Br)cnc1-c1ncn(CC(F)(F)C(F)(F)F)c1C] | amorphous |
| c-5 | 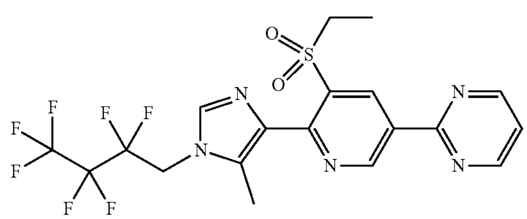 [SMILES: CCS(=O)(=O)c1cc(-c2ncccn2)cnc1-c1ncn(CC(F)(F)C(F)(F)C(F)(F)F)c1C] | m.p.: 97-99 (° C.) |
| c-6 | 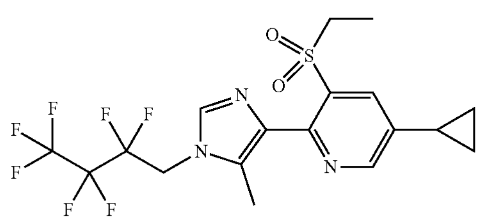 [SMILES: CCS(=O)(=O)c1cc(C2CC2)cnc1-c1ncn(CC(F)(F)C(F)(F)C(F)(F)F)c1C] | m.p.: 113-115 (° C.) |
| c-7 | 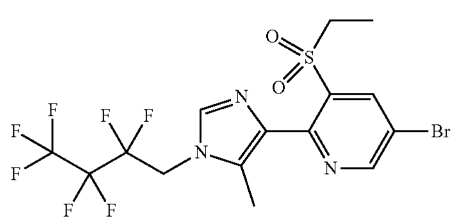 [SMILES: CCS(=O)(=O)c1cc(Br)cnc1-c1ncn(CC(F)(F)C(F)(F)C(F)(F)F)c1C] | m.p.: 98-100 (° C.) |

TABLE 3-continued

| Compound No. | Structure | Physical properties |
|---|---|---|
| c-8 | 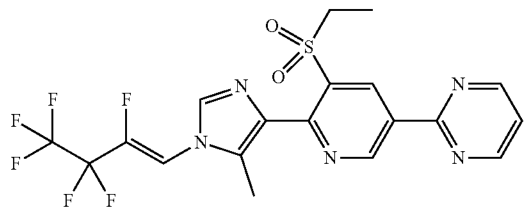 [SMILES: CCS(=O)(=O)c1cc(-c2ncccn2)cnc1-c1ncn(/C=C(\F)C(F)(F)C(F)(F)F)c1C] | m.p.: 208-210 (° C.) |
| c-9 | 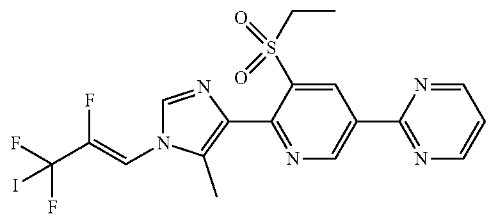 [SMILES: CCS(=O)(=O)c1cc(-c2ncccn2)cnc1-c1ncn(/C=C(\F)C(F)(F)I)c1C] | m.p.: 243-245 (° C.) |
| c-10 | 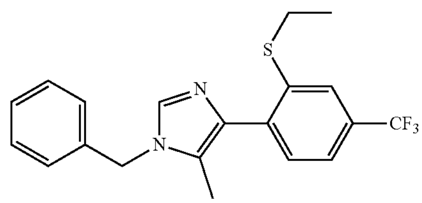 [SMILES: CCSc1cc(C(F)(F)F)ccc1-c1ncn(Cc2ccccc2)c1C] | m.p.: 118-120 (° C.) |
| c-11 | 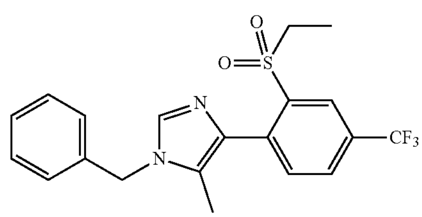 [SMILES: CCS(=O)(=O)c1cc(C(F)(F)F)ccc1-c1ncn(Cc2ccccc2)c1C] | m.p.: 132-135 (° C.) |

TABLE 4-1

| Compound No. | Structure | Physical properties |
|---|---|---|
| d-1 | 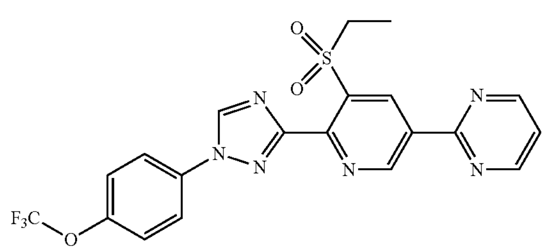 [SMILES: CCS(=O)(=O)c1cc(-c2ncccn2)cnc1-c1ncn(-c2ccc(OC(F)(F)F)cc2)n1] | PALE YELLOW SOLID |
| d-2 | 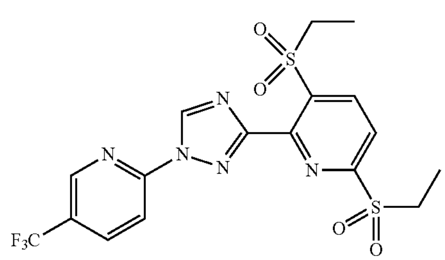 [SMILES: CCS(=O)(=O)c1ccc(S(=O)(=O)CC)c(-c2ncn(-c3ccc(C(F)(F)F)cn3)n2)n1] | m.p.: 152-155 (° C.) |

TABLE 4-1-continued

| Compound No. | Structure | Physical properties |
| --- | --- | --- |
| d-3 | 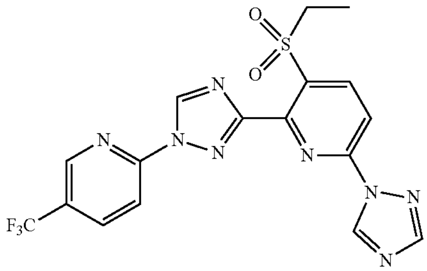 [SMILES: CCS(=O)(=O)c1ccc(-n2cncn2)nc1-c1ncn(-c2ccc(C(F)(F)F)cn2)n1] | m.p.: 196-199 (° C.) |
| d-4 | 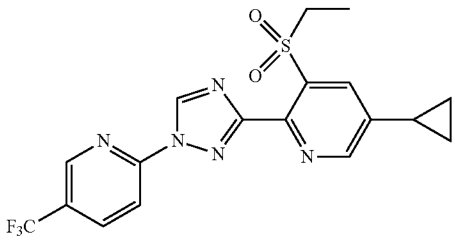 [SMILES: CCS(=O)(=O)c1cc(C2CC2)cnc1-c1ncn(-c2ccc(C(F)(F)F)cn2)n1] | m.p.: 193-195 (° C.) |
| d-5 | 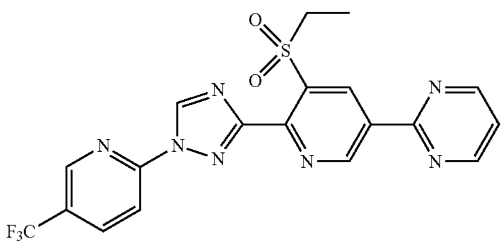 [SMILES: CCS(=O)(=O)c1cc(-c2ncccn2)cnc1-c1ncn(-c2ccc(C(F)(F)F)cn2)n1] | m.p.: 248-250 (° C.) |
| d-6 | 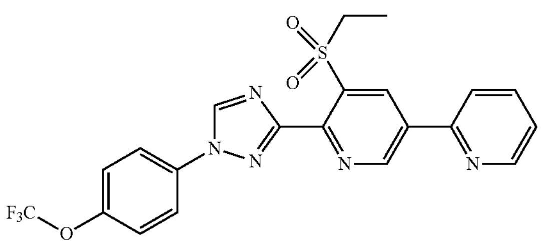 [SMILES: CCS(=O)(=O)c1cc(-c2ccccn2)cnc1-c1ncn(-c2ccc(OC(F)(F)F)cc2)n1] | m.p.: 232-234 (° C.) |
| d-7 | 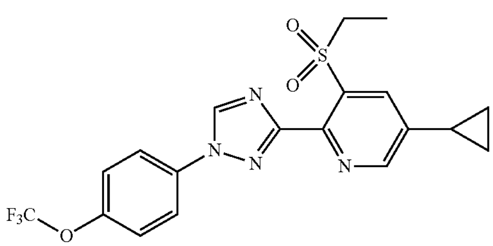 [SMILES: CCS(=O)(=O)c1cc(C2CC2)cnc1-c1ncn(-c2ccc(OC(F)(F)F)cc2)n1] | m.p.: 110-112 (° C.) |
| d-8 | 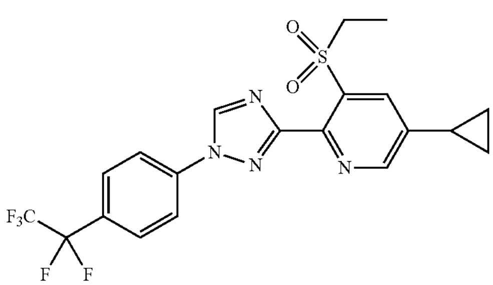 [SMILES: CCS(=O)(=O)c1cc(C2CC2)cnc1-c1ncn(-c2ccc(C(F)(F)C(F)(F)F)cc2)n1] | m.p.: 135-139 (° C.) |

TABLE 4-1-continued

| Compound No. | Structure | Physical properties |
|---|---|---|
| d-9 | 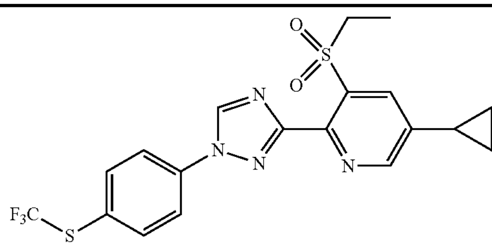 | m.p.: 146-148 (° C.) |
| d-10 | 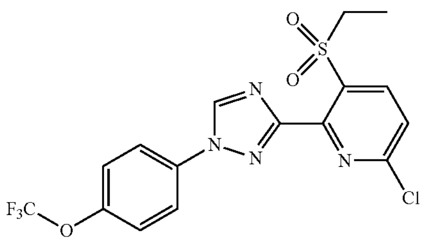 [SMILES: CCS(=O)(=O)c1ccc(Cl)nc1-c1ncn(-c2ccc(OC(F)(F)F)cc2)n1] | m.p.: 72-74 (° C.) |

TABLE 4-2

| d-11 | | m.p.: 226-228 (° C.) |
|---|---|---|
| d-12 | | m.p.: 106-108 (° C.) |
| d-13 | | m.p.: 88-90 (° C.) |

TABLE 4-2-continued

| | | |
|---|---|---|
| d-14 | (structure) | m.p.: 113-115 (° C.) |
| d-15 | (structure) | m.p.: 142-144 (° C.) |
| d-16 | (structure) | m.p.: 204-206 (° C.) |
| d-17 | (structure) | m.p.: 162-164 (° C.) |
| d-18 | (structure) | m.p.: 245-247 (° C.) |
| d-19 | (structure) | m.p.: 120-122 (° C.) |

TABLE 4-2-continued

| | | |
|---|---|---|
| d-20 | [structure] | m.p.: 199-201 (° C.) |

TABLE 4-3

| | | |
|---|---|---|
| d-21 | [structure] | m.p.: 208-210 (° C.) |
| d-22 | [structure] | m.p.: 185-187 (° C.) |
| d-23 | [structure] | m.p.: 165-167 (° C.) |
| d-24 | [structure] | m.p.: 161-163 (° C.) |

TABLE 4-3-continued

| | | |
|---|---|---|
| d-25 | [structure with methylsulfonyl pyridine-pyridine, imidazole, 4-(trifluoromethoxy)phenyl] | m.p.: 152-154 (° C.) |
| d-26 | [structure with methylsulfonyl pyridine-triazole, bromo-imidazole, 4-(trifluoromethoxy)phenyl] | m.p.: 198-200 (° C.) |
| d-27 | [structure with methylsulfonyl pyridine-triazole, methyl-imidazole, 4-(trifluoromethoxy)phenyl] | m.p.: 236-238 (° C.) |

The $^1$H-NMR data of compounds having physical properties of viscous oil or amorphous among the compounds shown in Tables 1 to 3 will be shown below.

Compound No. (a-18): $^1$H-NMR (400 MHz, CDCl$_3$): δ 9.06 (1H, s), 8.71 (1H, s), 7.59 (1H, s), 4.05 (2H, q), 2.49 (3H, s), 1.38 (3H, t).

Compound No. (a-19): $^1$H-NMR (400 MHz, CDCl$_3$): δ 9.09 (1H, s), 8.71 (1H, s), 7.74 (1H, s), 6.40 (1H, d), 3.97 (2H, q), 2.50 (3H, s), 1.36 (3H, t).

Compound No. (b-21): $^1$H-NMR (400 MHz, CDCl$_3$): δ 8.72 (2H, dd), 8.05 (1H, d), 7.38 (1H, d), 6.10 (1H, tt), 3.88 (2H, q), 2.12-2.04 (1H, m), 1.37 (3H, t), 1.30-1.16 (2H, m), 0.96-0.87 (2H, m).

Compound No. (b-23): $^1$H-NMR (400 MHz, CDCl$_3$): δ 8.73 (1H, d), 8.62 (1H, s), 8.06 (1H, d), 6.65 (1H, ddd), 3.76 (2H, q), 2.12-2.05 (1H, m), 1.36 (3H, t), 1.26-1.21 (2H, m), 0.93-0.89 (2H, m).

Compound No. (c-4): $^1$H-NMR (400 MHz, CDCl$_3$): δ 8.85 (d, 1H), 8.57 (d, 1H), 7.54 (s, 1H), 4.48 (t, 2H), 3.95 (q, 2H), 2.37 (s, 3H), 1.33 (t, 3H).

[Biological Test]

Test Examples given below show that the heteroaryl azole compound of the present invention is useful as an active ingredient for pest control agents and ectoparasite control agents. The term "part" is based on weight.

(Preparation of Test Emulsion)

5 parts of the heteroaryl azole compound of the present invention, 93.6 parts of dimethylformamide, and 1.4 parts of polyoxyethylene alkyl aryl ether were mixed and dissolved to prepare emulsion (I) containing 5% of the active ingredient.

For a control, 98.5 parts of dimethylformamide and 1.5 parts of polyoxyethylene alkyl aryl ether were mixed and dissolved to prepare emulsion (II).

An insecticidal rate was calculated according to the following expression:

Insecticidal rate (%)=(The number of dead insects/ The number of tested insects)×100

(Test Example 1) Test of Efficacy on *Mythimna separata*

0.8 g of commercially available artificial feed (Insecta LFS, manufactured by Nosan Corp.) and 1 μl of the emulsion (I) were well mixed to obtain test feed.

A plastic test container (capacity: 1.4 ml) was packed with 0.2 g of the test feed per treatment plot. Then, two second instar larvae of *Mythimna separata* were inoculated to each treatment plot. A plastic lid was put on the test container so as to prevent escape of the second instar larvae of *Mythimna separata*. The container was placed in a thermostat chamber of 25° C. On the fifth day, the insecticidal rate and the food intake were examined. The test was conducted in duplicate.

The insecticidal rate and the food intake of a control plot were examined in the same way as in Test Example 1 except that the emulsion (I) was changed to the emulsion (II).

Compounds of compound Nos. a-4, a-5, a-14, a-15, a-16, a-17, b-3, b-10, b-12, b-20, b-22, c-1, c-2, c-5, c-6, d-3, d-4, d-5, d-6, d-9, d-10, d-11, d-13, d-14, d-15, d-16, d-19, d-20, d-24, d-25, d-26, and d-27 were tested for their efficacy on *Mythimna separata*. All the compounds had an insecticidal rate of 100% for *Mythimna separata* or a food intake of 10% or less as compared with the control plot. As is evident, the heteroaryl azole compound of the present invention is effective for *Mythimna separata*.

(Test Example 2) Test of Efficacy on *Plutella xylostella*

The emulsion (I) was diluted with water such that the concentration of the compound of the present invention was 125 ppm. Cabbage leaves were dipped in the dilution for 30 seconds. The resulting cabbage leaves were placed in a petri dish. Five second instar larvae of *Plutella xylostella* were released thereto. The petri dish was placed in a thermostat chamber having a temperature of 25° C. and a humidity of 60%. Life and death were determined after 3 days from the release of the insects, and the insecticidal rate was calculated. The test was conducted in duplicate.

Compounds of compound Nos. a-3, a-4, a-13, a-14, a-15, a-16, a-17, b-3, b-10, b-12, b-21, b-22, b-25, c-5, c-8, c-9, d-1, d-4, d-5, d-6, d-7, d-15, d-16, d-19, d-20, d-22, d-23, d-24, d-25, d-26 and d-27 were tested for their efficacy on *Plutella xylostella*. All the compounds exhibited an insecticidal rate of 80% or more for *Plutella xylostella*.

(Test Example 3) Test of Efficacy on *Aphis craccivora*

Seedlings of black-eyed peas were raised in 10-cm pots. *Aphis craccivora* nymphs were inoculated onto primary leaves. The emulsion (I) was diluted with water such that the concentration of the compound of the present invention was 125 ppm. The dilution was sprayed to the black-eyed peas parasitized by the *Aphis craccivora* nymphs. The black-eyed peas were placed in a thermostat chamber having a temperature of 25° C. and a humidity of 60%. Life and death of *Aphis craccivora* were determined after 4 days from the spraying, and the insecticidal rate was calculated. The test was conducted in duplicate.

Compounds of compound Nos. a-4, a-5, a-6, a-7, a-8, a-9, a-10, a-14, a-15, a-16, a-17, b-3, b-4, b-5, b-8, b-10, b-12, b-13, b-14, b-20, b-22, b-23, b-24, b-25, c-1, c-2, c-3, c-4, c-5, c-6, c-7, d-3, d-4, d-6, d-10, d-11, d-14, d-16, d-18, d-19, d-20, d-21, d-22, d-24, d-25, d-26, and d-27 were tested for their efficacy on *Aphis craccivora*. All the compounds exhibited an insecticidal rate of 80% or more for *Aphis craccivora*.

(Test Example 4) Test of Efficacy on *Phyllotreta striolata*

The emulsion (I) was diluted with water such that the concentration of the compound of the present invention was 125 ppm to prepare a test chemical. The test chemical was sprayed to Qing geng cai seedlings (at the seventh true leaf stage) planted in 10-cm pots. The Qing geng cai seedlings were dried in air and then placed in a plastic cup. Ten *Phyllotreta striolata* adults were released thereto. The plastic cup was stored in a thermostat chamber having a temperature of 25° C. and a humidity of 65%. Life and death were determined after 7 days from the release of the insects, and the insecticidal rate was calculated. The test was conducted in duplicate.

Compounds of compound Nos. a-3, a-13, a-14, b-3, b-8, b-10, b-12, b-13, c-5, c-8, c-9, d-1, d-6, d-7, d-19, d-20, and d-22 were tested for their efficacy on *Phyllotreta striolata* adults. All the compounds exhibited an insecticidal rate of 80% or more for *Phyllotreta striolata* adults.

(Test Example 5) Test of Efficacy on *Nilaparvata lugens*

The emulsion (I) was diluted with water such that the concentration of the compound of the present invention was 125 ppm. Young seedlings of rice were dipped in the dilution for 30 seconds. The young seedlings of rice were dried in air and then placed in a plastic case. Five second instar larvae of *Nilaparvata lugens* were released thereto. The plastic case was stored in a thermostat chamber having a temperature of 25° C. and a humidity of 65%. Life and death were determined after 7 days from the inoculation, and the insecticidal rate was calculated. The test was conducted in duplicate.

Compounds of compound Nos. a-3, a-4, a-13, a-17, c-8, c-9 and d-25 were tested for their efficacy on *Nilaparvata lugens*. All the compounds exhibited an insecticidal rate of 80% or more for *Nilaparvata lugens*.

All the compounds selected at random from among the heteroaryl azole compounds of the present invention exerted the effect as described above. It may therefore be understood that the heteroaryl azole compound of the present invention, including unillustrated compounds, is a compound having an effect such as a pest control effect, particularly, a miticidal or insecticidal effect. It may also be understood that the heteroaryl azole compound of the present invention is a compound also having an effect on parasites harmful to humans and animals, such as ectoparasites.

The invention claimed is:

1. A compound of formula (II), an N-oxide compound, stereoisomer, tautomer or hydrate thereof, or a salt of any of these compounds:

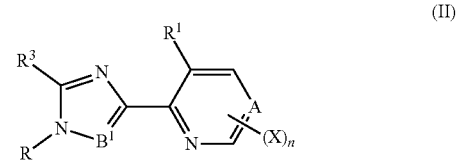

(II)

wherein $R^1$ represents a substituted or unsubstituted C1-6 alkylthio group, a substituted or unsubstituted C1-6 alkylsulfinyl group or a substituted or unsubstituted C1-6 alkylsulfonyl group;

$B^1$ represents a nitrogen atom or $CR^2$;

$R^2$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted amino group, a cyano group or a halogeno group;

$R^3$ represents a hydrogen atom, a substituted or unsubstituted C1-6 alkyl group or a halogeno group;

R represents a C1-6 haloalkyl group, a C1-6 haloalkoxy C1-6 haloalkyl group, a C2-6 haloalkenyl group, or a C1-6 haloalkoxy C2-6 haloalkenyl group;

A represents a carbon atom or a nitrogen atom;

X represents a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C1-6 alkoxycarbonyl group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-8 cycloalkyl group, a substituted or unsubstituted C6-10 aryl group, a substituted or unsubstituted 5- to 6-membered heteroaryl group, a substituted or unsubstituted C6-10 aryloxy group, a substituted or unsubstituted 5- to 6-membered heteroaryloxy group, a substituted or unsubstituted amino group, a substituted or unsubstituted aminocarbonyl group, a substituted or unsubstituted hydrazinyl group, a nitro group, a cyano group or a halogeno group;

n represents a number of chemically acceptable X, and is an integer of 0 to 2; and X is the same or different when n is 2.

2. A pest control agent comprising at least one active ingredient selected from the group consisting of a compound according to claim 1, an N-oxide compound, stereoisomer, tautomer and hydrate thereof and a salt of any of these compounds.

3. An insecticide or acaricide comprising at least one active ingredient selected from the group consisting of a compound according to claim 1, an N-oxide compound, stereoisomer, tautomer and hydrate thereof and a salt of any of these compounds.

4. An ectoparasite control agent comprising at least one active ingredient selected from the group consisting of a compound according to claim 1, an N-oxide compound, stereoisomer, tautomer and hydrate thereof and a salt of any of these compounds.

5. An endoparasite control agent or expellant comprising at least one active ingredient selected from the group consisting of a compound according to claim 1, an N-oxide compound, stereoisomer, tautomer and hydrate thereof and a salt of any of these compounds.

* * * * *